(12) United States Patent
Guillén et al.

(10) Patent No.: US 12,046,335 B2
(45) Date of Patent: *Jul. 23, 2024

(54) PATIENT CALLBACK TOOL AND INTERFACE

(71) Applicant: MedAmerica Data Services, LLC, Emeryville, CA (US)

(72) Inventors: Jimmy Guillén, Oakland, CA (US); Travis Payne, San Francisco, CA (US); Jenny Hyun, San Jose, CA (US); Vivek Bhansali, San Jose, CA (US); Amy Baer, Albany, CA (US); Justin Plumley, Durham, NC (US); Dipti Patel-Misra, Alamo, CA (US); Joshua Tamayo-Sarver, Los Gatos, CA (US)

(73) Assignee: MEDAMERICA DATA SERVICES, LLC, Emeryville, CA (US)

(*) Notice: Subject to any disclaimer, the term of this patent is extended or adjusted under 35 U.S.C. 154(b) by 0 days.

This patent is subject to a terminal disclaimer.

(21) Appl. No.: 17/981,370

(22) Filed: Nov. 4, 2022

(65) Prior Publication Data
US 2024/0096459 A1   Mar. 21, 2024

Related U.S. Application Data

(63) Continuation of application No. 16/378,542, filed on Apr. 8, 2019, now Pat. No. 11,501,859.
(Continued)

(51) Int. Cl.
*G16H 10/60* (2018.01)
*A61B 5/00* (2006.01)
(Continued)

(52) U.S. Cl.
CPC ............. *G16H 10/60* (2018.01); *G16H 40/40* (2018.01); *G16H 50/30* (2018.01); *A61B 5/0022* (2013.01); *G06F 3/0482* (2013.01); *H04L 67/12* (2013.01)

(58) Field of Classification Search
CPC ........ G16H 10/60; G16H 50/30; G16H 40/40; A61B 5/0022; G06F 3/0482; H04L 67/12
(Continued)

(56) References Cited

U.S. PATENT DOCUMENTS

| 8,417,533 B2 | 4/2013 | Clawson |
| 9,092,964 B1 * | 7/2015 | Chan ...................... G16H 70/60 |

(Continued)

FOREIGN PATENT DOCUMENTS

| CA | 2 777 838 A1 | 4/2011 | |
| EP | 2560110 A1 * | 2/2013 | ........... G06F 16/313 |

(Continued)

OTHER PUBLICATIONS

Soto, Gabriel E et al.; Implementation and impact analysis of a transitional care pathway for patients presenting to the emergency department with cardiac-related complaints; BMC Health Services Research 18 BioMed Central. (2018) (Year: 2018).*

(Continued)

*Primary Examiner* — Hiep V Nguyen
(74) *Attorney, Agent, or Firm* — MASCHOFF BRENNAN; Elaine K. Lee

(57) ABSTRACT

A user interface for a physician or other health care provider to follow up with high-risk patients recently discharged from the emergency department (ED) and update the patient's health care record using the physician or provider's mobile or end user device is described. The user interface is generated after extracting patient detail batch information at a pre-defined time interval for one or more past patients from
(Continued)

an electronic medical records (EMR) database or other patient information database into a medical activity tracking batch database, and constructing a real-time database from streams of real-time Health Level 7 (HL7) clinical administrative data, wherein at least one stream of real-time HL7 clinical administrative data is associated with at least one high-risk patient in a recent medical encounter and at least one stream of real-time HL7 data comprises daily schedule information associating at least one clinician with the at least one high-risk patient.

20 Claims, 12 Drawing Sheets

Related U.S. Application Data

(60) Provisional application No. 62/701,137, filed on Jul. 20, 2018.

(51) Int. Cl.
    *G06F 3/0482*     (2013.01)
    *G16H 40/40*     (2018.01)
    *G16H 50/30*     (2018.01)
    *H04L 67/12*     (2022.01)

(58) Field of Classification Search
    USPC .......................................................... 705/3
    See application file for complete search history.

(56) References Cited

U.S. PATENT DOCUMENTS

| | | | |
|---|---|---|---|
| 9,177,106 | B2 | 11/2015 | Smith et al. |
| 11,177,041 | B1 | 11/2021 | Sutton et al. |
| 2004/0078236 | A1 | 4/2004 | Stoodley et al. |
| 2004/0087864 | A1 | 5/2004 | Grouse |
| 2007/0168223 | A1 | 7/2007 | Fors et al. |
| 2008/0154642 | A1 | 6/2008 | Marble et al. |
| 2008/0255885 | A1 | 10/2008 | Eisenberger et al. |
| 2012/0029932 | A1 | 2/2012 | Stein et al. |
| 2012/0215560 | A1 | 8/2012 | Ofek et al. |
| 2012/0323588 | A1 | 12/2012 | Kelly et al. |
| 2013/0332194 | A1 | 12/2013 | D'Auria et al. |
| 2014/0236626 | A1 | 8/2014 | Reddy Bynagari |
| 2014/0297302 | A1 | 10/2014 | Vanier et al. |
| 2015/0213224 | A1 | 7/2015 | Amarasingham et al. |
| 2015/0287317 | A1 | 10/2015 | Chan et al. |
| 2015/0339791 | A1 | 11/2015 | Tetteh |
| 2016/0063209 | A1 | 3/2016 | Malaviya |
| 2016/0321426 | A1* | 11/2016 | Bhatt ................. G06F 40/10 |
| 2016/0364544 | A1 | 12/2016 | Das et al. |
| 2017/0006135 | A1 | 1/2017 | Siebel et al. |
| 2017/0061093 | A1 | 3/2017 | Amarasingham et al. |
| 2017/0091388 | A1 | 3/2017 | Zolla et al. |
| 2017/0277732 | A1 | 9/2017 | Dwire et al. |

FOREIGN PATENT DOCUMENTS

| | | |
|---|---|---|
| KR | 10-2014-0034618 A | 3/2014 |
| WO | 2014/042942 A1 | 3/2014 |
| WO | 2014/100736 A2 | 6/2014 |
| WO | 2017/091603 A1 | 6/2017 |
| WO | WO-2017091603 A1 * | 6/2017 ............. G06N 20/00 |

OTHER PUBLICATIONS

Tripp, Jacob Stewart; Development and evaluation of notifications to inform primary care providers of summary documentation for their patients' hospital visits; The University of Utah. ProQuest Dissertations Publishing, 2009. 3353943. (Year: 2009).*
Bhansali et al., U.S. Appl. No. 16/297,456, entitled Real Time Parser for Use With Electronic Medical Records, filed Mar. 8, 2019.
Guillén et al., U.S. Appl. No. 16/378,542, entitled Patient Callback Tool and Interface, filed Apr. 8, 2019.
Bhansali et al., U.S. Appl. No. 16/378,439, entitled Patient Trackerboard Tool and Interface, filed Apr. 8, 2019.
Hsia et al., "A National Study of the Prevalence of Life-Threatening Diagnoses in Patients with Chest Pain," JAMA Internal Medicine, 2016, vol. 176, No. 7, pp. 1029-1032.
Antman et al., "The TIMI Risk Score for Unstable Angina/Non-ST Elevation MI, a Method for Prognostication and Therapeutic Decision Making," American Medical Association, 2000, vol. 284, No. 7, pp. 835-842.
Lagerqvist et al., "FRISC score for selection of patients for an early invasive treatment strategy in unstable coronary artery disease," Heart, 2005, vol. 91, No. 8, pp. 1047-1052.
Six et al., "Chest pain in the emergency room: value of the HEART score," Netherlands Heart Journal, 2008, vol. 16, pp. 191-196.
Cervellin et al., "Diagnostic algorithms for acute coronary syndrome—is one better than another?," Annals of Translational Medicine, 2016, vol. 4, No. 10, 6 pages.
Goodacre et al., "The health care burden of acute chest pain," Heart, 2005, vol. 91, No. 2, pp. 229-230.
Goodacre et al., "Cost effectiveness of diagnostic strategies for patients with acute, undifferentiated chest pain," Emergency Medicine Journal, 2003, vol. 20, No. 5, pp. 429-433.
Penumetsa et al., "Outcomes of Patients Admitted for Observation of Chest Pain," Archives of Internal Medicine, 2012, vol. 172, No. 11, pp. 873-877.
Sharif et al., "Does This Patient With Chest Pain Have Acute Coronary Syndrome?," Annals of Emergency Medicine 2017, vol. 70, No. 1, pp. 44-45.
Tang et al., "Global Registry of Acute Coronary Events (GRACE) hospital discharge risk score accurately predicts long-term mortality post acute coronary syndrome," American Heart Journal, 2007, vol. 153, No. 1 pp. 29-35.
Than et al., "What is an acceptable risk of major adverse cardiac event in chest pain patients soon after discharge from the Emergency Department? A clinical survey," International Journal of Cardiology, 2012, vol. 166, No. 3, pp. 752-754.
Rajkomar et al., "Scalable and accurate deep learning with electronic health records," NPJ Digital Medicine, 2018, 10 pages.
Chatterjee et al., "HL7 FHIR with SNOMED-CT to Achieve Semantic and Structural Interoperability in Personal Health Data: A Proof-of-Concept Study," Sensors, 2022, vol. 22, No. 10, 48 pages.
Mochão et al. "IPOscore: An interactive web-based platform for postoperative surgical complications analysis and prediction in the oncology domain," Computer Methods and Programs in Biomedicine, 2022, vol. 219, 15 pages.
Weiss et al. "Machine learning for personalized medicine: predicting primary myocardial infarction from electronic health records," AI Magazine, 2012, vol. 33, No. 4, pp. 33-45.
Alqudah et al., "Medical data integration using HL7 standards for patient's early identification," Plos one, vol. 16, No. 12, 2021, 16 pages.
Bhansali et al., U.S. Appl. No. 17/971,534, entitled Patient Trackerboard Tool and Interface, filed Oct. 21, 2022.
Sutton et al., U.S. Appl. No. 17/751,339, entitled Method and System for Cardic Risk Assessment of a Patient Using Historical and Real-Time Data, filed Oct. 26, 2021.

* cited by examiner

| Patient Name | MRN | Encounter # | ED Arrival | ED Visits Last 6 Mo | Last ED Visit | Attending Provider |
|---|---|---|---|---|---|---|
| Doe, John (72) | XYZ1234 | ABC12345 | 5/31/2517 13:04 | 1 | | Jones, Sarah |
| ⋮ | ⋮ | ⋮ | ⋮ | ⋮ | ⋮ | ⋮ |
| ⋮ | ⋮ | ⋮ | ⋮ | ⋮ | ⋮ | ⋮ |
| ⋮ | ⋮ | ⋮ | ⋮ | ⋮ | ⋮ | ⋮ |
| Li, Jane (39) | XYZ1239 | ABD32112 | 5/31/2517 13:06 | 35 | 5/15/2517 18:25 | |
| ⋮ | ⋮ | ⋮ | ⋮ | ⋮ | ⋮ | ⋮ |
| ⋮ | ⋮ | ⋮ | ⋮ | ⋮ | ⋮ | ⋮ |
| ⋮ | ⋮ | ⋮ | ⋮ | ⋮ | ⋮ | ⋮ |

ED Trackerboard List for May 31, 2517 13:20

Control Panel
All Sites 500
510
520
530
540
550
560
570
580
590

THOMAS, DESIREE (34)

HEAD PAIN
Reason for Visit

MEDICARE
Payer Type

05/26 16:45
Time of Discharge

ZHMA184     ENC999169
MRN          Encounter #

825 — Call     Destiny — 830

Callback Outcome*
[ ▼ ] — 840

Patient Status*
[ ▼ ] — 850

Comments
[ ] — 860

Submit — 870

Powered by Vituity

PATIENT CALLBACK TOOL AND INTERFACE

CROSS REFERENCE TO RELATED APPLICATIONS

This application is a continuation of U.S. Non-Provisional application Ser. No. 16/378,542 filed Apr. 8, 2019, which claims benefit of U.S. Provisional Application No. 62/701,137, filed Jul. 20, 2018. The entire content of these applications is hereby incorporated herein by reference.

BACKGROUND

The present technology relates generally to electronic records maintained by hospitals and other health care facilities for patients and used by those providing health care services to the patients, such as physicians and other clinicians working in the hospitals, clinics and other health care facilities. Such electronic records may be stored and maintained by hospitals and health care facilities as part of health care computing systems, such as Electronic Medical Record (EMR) and Electronic Health Record (EHR) related technology (herein, the term "EMR" is intended to include both EMR and EHR).

For patients admitted to hospitals for treatment, such as patients admitted to hospital emergency departments, for example, health care providers often desire or are expected to conduct follow-up calls on patients after discharge. Clinicians may particularly wish to or be expected to conduct follow-up calls for patients with known risk factors or health conditions. Prior to this invention, health care providers had to manually identify patients for necessary follow up, and/or print out patient lists with patient phone numbers or use patient stickers to track their patients. Then, for sites with incentives for callbacks, providers would often be required to log those calls, and any outcomes, resolutions, or follow up notes in a separate spreadsheet.

Disadvantages of this manual process potentially include provider time taken in generating patient lists and logging completed calls, potential error by the health care provider in the manual identification of patients and manual entry of follow up notes, as well as privacy concerns with patient stickers and patient lists on paper floating around.

SUMMARY

One potential goal of an automated call back program as developed in embodiments of the present invention as described in the below could be to foster positive patient outcomes and to improve the overall patient experience. A call back tool suite as described in some embodiments of the present invention could be designed and engineered to deliver a simplified, provider-centric solution for completing and tracking post-visit follow-up phone calls to patients.

Some embodiments of the present invention allow health care providers (e.g. physicians or other clinicians, or their designees such as medical scribes) to deploy a mobile application that will create an automatically generated list of patients that have been recently discharged from the emergency department to call back for follow up. Some embodiments of the present invention are further configured to allow health care providers to automatically dial each patient on the list, enter notes, and/or track completed phone calls. A trackerboard functionality available in some embodiments of the present invention allow health care providers or scribes to "add" patients to their callback lists in real-time, i.e., as patients are in the hospital or being discharged from the hospital. This functionality for a trackerboard available in some embodiments of the present invention allows each health care provider to make custom lists for their own callbacks. Functionality available in some embodiments of the present invention in mobile as well as desktop versions allows providers to make phone calls directly from their cell phones or via VoIP or Wi-Fi calling capabilities on their laptop or desktop computers or other computing devices.

Embodiments of the present invention describe a patient callback tool which is populated with patients specific for the physician, including high-risk patients or other patients designated for follow-up, within 24 hours of the end of a shift for the specific physician. In some embodiments of the invention, the patient callback tool lets the physician dial the phone and mask their cell number using Doximity dialer or other phone number automated dialing and caller ID masking methods or tools. In some embodiments of the invention, the patient callback tool is configured to receive output or feedback entered by the physician from or during the call back. The output and feedback collected from the physician is collected into a database and a dashboard is populated in real time.

BRIEF DESCRIPTION OF THE DRAWINGS

FIG. 5 illustrates a screenshot of an exemplary user interface display according to some embodiments of the invention;

FIG. 8 illustrates a screenshot of an exemplary user interface display according to some embodiments of the invention;

Figure 1:
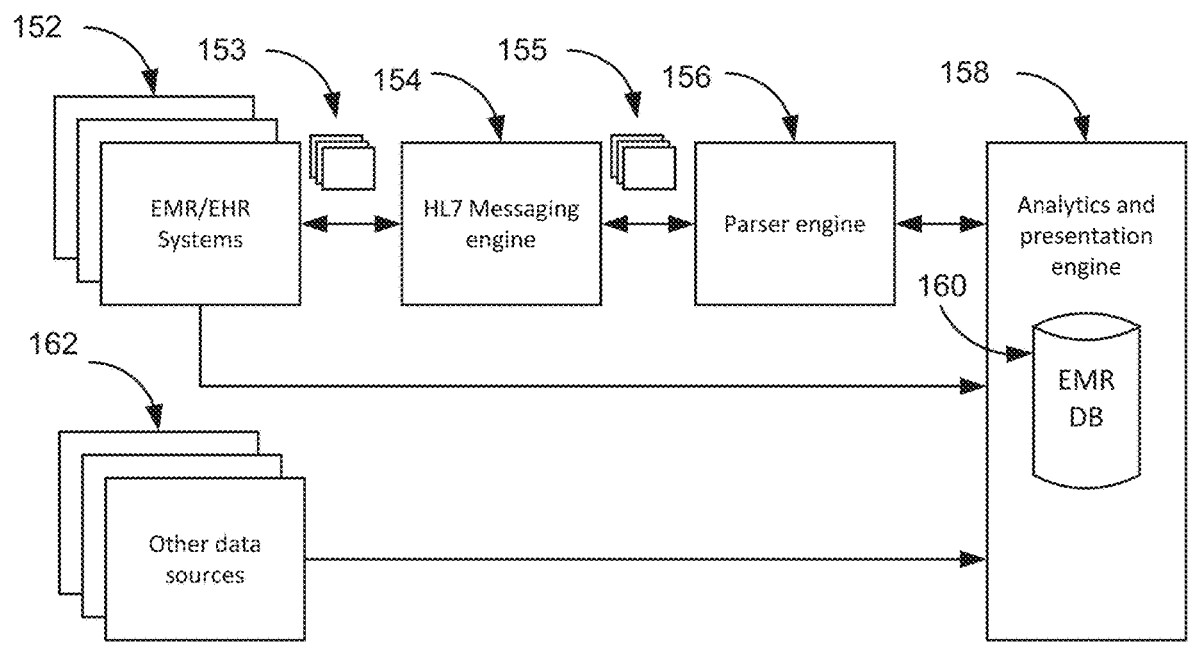
FIG. 1 illustrates a block diagram of an architecture of a system according to some embodiments of the invention, including an HL7 messaging engine and a parser engine.

While the invention is described with reference to the above drawings, the drawings are intended to be illustrative, and the invention contemplates other embodiments within the spirit of the invention.

DETAILED DESCRIPTION

The following description is presented to enable any person skilled in the art to make and use embodiments of the invention and is provided in the context of particular applications and their requirements. Various modifications to the exemplary embodiments will be readily apparent to those skilled in the art, and the generic principles defined herein may be applied to other embodiments and applications without departing from the spirit and scope of the invention. Thus, the present invention is not intended to be limited to the embodiments shown but is to be accorded the widest scope consistent with the principles and features disclosed herein.

The present invention will now be described more fully hereinafter with reference to the accompanying drawings which show, by way of illustration, specific embodiments by which the invention may be practiced. This invention may, however, be embodied in many different forms and should not be construed as limited to the embodiments set forth herein; rather, these embodiments are provided so that this disclosure will be thorough and complete, and will fully convey the scope of the invention to those skilled in the art. Among other things, the present invention may be embodied as devices or methods. Accordingly, the present invention may take the form of an entirely hardware embodiment, an entirely software embodiment, or an embodiment combining software and hardware aspects. The following detailed description is, therefore, not to be taken in a limiting sense.

Throughout the specification and claims, the following terms take the meanings explicitly associated herein, unless the context clearly dictates otherwise. The phrases "in one embodiment," "in an embodiment," and the like, as used herein, does not necessarily refer to the same embodiment, though it may. Furthermore, the phrase "in another embodiment" as used herein does not necessarily refer to a different embodiment, although it may. Thus, as described below, various embodiments of the invention may be readily combined, without departing from the scope or spirit of the invention.

In addition, as used herein, the term "or" is an inclusive "or" operator and is equivalent to the term "and/or," unless the context clearly dictates otherwise. The term "based on" is not exclusive and allows for being based on additional factors not described, unless the context clearly dictates otherwise. In addition, throughout the specification, the meaning of "a," "an," and "the" includes plural references. The meaning of "in" includes "in" and "on."

It is noted that description herein is not intended as an extensive overview, and as such, concepts may be simplified in the interests of clarity and brevity.

Any process described in this application may be performed in any order and may omit any of the steps in the process. Processes may also be combined with other processes or steps of other processes.

FIG. 1 illustrates a block diagram of an architecture 150 of a system according to some embodiments of the invention. Depicted are multiple EMR/EHR systems 152, other data sources 162, an HL7 messaging engine 154, a parser engine 156 and an analytics and presentation engine 158. In various embodiments, elements such as the EMR/EHR systems 152, the other data sources 162 and the HL7 messaging engine 154, or portions thereof, may or may not themselves be part of the inventive system. For example, in some embodiments, the parser engine 156 only, or operation thereof, or elements of the parser engine 156, or elements of operation thereof, may constitute an entire inventive system, method, apparatus, architecture, data structure, computer readable media, etc.

It is to be understood that intermediary entities may be present in addition to those depicted, or multiple separate sub-entities of particular entities, and data may be received and sent from such non-depicted intermediaries or sub-entities to, from or within depicted entities, such as from the EMR/EHR systems 152 or the other data sources 162. It is further to be understood that, while a single HL7 messaging engine 154, parser engine 156 and analytics and presentation engine 158 are depicted, each engine can be implemented by or using one or more networks, computers, servers, clients, applications, operating systems, software, hardware, etc., as well as various communications therebetween. Other patent applications describe exemplary embodiments of this HL7 messaging engine, real time parser engine, and analytics and presentation engine in detail, including, but not limited to, co-pending U.S. patent application Ser. No. 16/297,456 for "Real Time Parser for Use with Electronic Medical Records", filed on Mar. 8, 2019, which is herein incorporated by reference in its entirety.

The EMR/EHR systems 152 may be located at or associated with various sites, such as hospitals, medical facilities, doctor's offices, etc. EMR data may be entered, logged, recorded or input at such sites. For example, upon admission of a patient into a hospital, EMR data relating to the patient, e.g. patent's name, patient's demographics, billing information, insurance information, health-related complaint, lab tests ordered for diagnosis, collected vitals or other data, and many other types of data, may be entered, recorded or logged, or collected and entered, recorded or logged, into the hospital's computerized EMR system. In addition, other types of EMR data may be entered.

EMR data entered or logged into the EMR/EHR systems 152 may immediately, such as in real time or near real time, be sent as a stream of data items or HL7 messages 153 to the HL7 messaging engine 154, directly, indirectly or via intermediary entities. Depending on specific circumstances, real time or near real time can be, for example, within seconds or a fraction of a second. In various embodiments, the EMR data sent from the EMR/EHR systems 152 may be in various forms and formats, such as not yet formatted into HL7 messages, partially formatted into HL7 messages, or fully formatted into HL7 messages.

In various embodiments, the HL7 messaging engine 154 may serve a variety of functions, such as relating to formatting, structuring or serializing, or re-formatting, re-structuring or re-serializing or sending, for example, EMR data not in the form of HL7 messages, partial or incompletely formatted or structured HL7 messages, or complete or fully structured HL7 messages. However, in some embodiments, an HL7 engine may be omitted, and HL7 messages may be sent directly or indirectly to the parser engine 156 without first being sent to an HL7 messaging engine 154. Furthermore, in some embodiments, the parser engine 156 alone, or certain elements thereof, may perform all inventive steps or may constitute the entire inventive architecture, method, system, computer readable media, etc. In other embodiments, the parser engine 156 or elements thereof, or other engines or elements other than the parser engine 156, may constitute the entire inventive architecture, method, system, computer readable media, etc.

In some embodiments, the HL7 messaging engine 154 may be implemented, in whole or in part, using various tools and designs, such as, for example, a Mirth or Mirth Connect or Nextgen Connect cross-platform HL7 interface engine.

In some embodiments, the HL7 messaging engine 154 plays a role in, for example standardizing, unifying, or otherwise preparing for efficient and fast ingestion by the parser engine 156 of all or part of disparate or variously structured or formatted EMR data or HL7 messages originating from the various EMR/EHR systems 152. This can include, for example, accounting for, labelling or otherwise preparing for ingestion by the parser engine 156 HL7 messages with custom or z-segments specified by particular EMR systems or sites 152. Although embodiments of the invention are described herein generally with reference to HL7 messages, in some embodiments, EMR data or messages other than HL7 messages, or non-medical electronic records, are contemplated and utilized.

As depicted, HL7 messages 155 are sent or streamed from the HL7 messaging engine 154 to the parser engine 156. The parser engine 156 may immediately parse the HL7 messages to identify, locate (such as, within an HL7 message) and extract (which can broadly include copying, duplicating, sending, making use of, etc.) particular HL7 message data, such as using parser logic that may, for example, be embodied in software. The parser engine 156 may direct storage of the extracted HL7 message data in an EMR database 160 of the analytics and presentation engine 158, such as by using relational database interface logic that may, for example, be embodied in software. However, in some embodiments, the directing of the extracted data may be accomplished in whole or in part outside of the parser engine 156, such as in whole or in part by the analytics and presentation engine 158. In some embodiments, the parser engine 156 may direct storage of extracted EMR data as appropriate, optimal or efficient, in tables of the EMR database 160, with logic considering the design and structure of the EMR database 160.

The EMR database 160 may be any of various types of data stores and databases and may or may not be a relational database. In some embodiments, various relational database management systems (RDBMS), tools, applications, programming and programming languages may be used in connection with the EMR database 160 and the directing of extracted data to and from the database 160, such as, for one of many possible examples, SQL (Structured Query Language). The EMR database 160, as well as database management and tools, may be designed and structured, in whole or in part, to accommodate, speed, make more efficient, or optimize its use according to embodiments of the invention.

For various clinical, medical, or health care related needs, requests or uses, the analytics and presentation engine 158 may query the EMR database 160 for needed EMR data. In some embodiments, the EMR database 160 may contain both real-time or near real time data represented as data that has passed through the parser engine 156, and other data, represented as data that has not passed through the parser engine 156. Furthermore, the analytics and presentation engine 158 may use, in determining analytic results data, for example, data from EMR/EHR systems 152 and data from other data sources 162. The utilized data may include data originating as HL7 message data and other data.

The analytics and presentation engine 158 may then analyze or direct analysis of acquired or selected EMR data to determine or generate needed analytical results data, which may be dependent on the use case scenario. The analytical results data may be presented, including made available for presentation, such as display, to, for example, doctors or other medical professionals or medical staff. In determining the analytical result data, the analytics and presentation engine may use logic embodied in software, and may utilize both current, real time or near real time EMR data as well as historical, chronologically tracked EMR data from the EMR database 160. Presentation or display of analytical results data case broadly include presentations or displays that directly or indirectly communicate portions, elements or aspects of the analytical results data, directly or indirectly, or data derived therefrom.

The EMR database 160 may be designed or structured, in whole or in part, to best accommodate its anticipated uses for clinical, medical, or health care related needs, requests or uses according to embodiments of the invention. For example, the tables, views and other structuring elements of the EMR database 160 may be designed and configured to best, quickly, efficiently or optimally enable determination of analytical results data, such as for particular clinical, medical, or health care related needs, requests or uses. For example, in some embodiments, tables that may receive extracted data may include one or more tables with each of patient data, patient encounter data, patient insurance data, insurance provider data, patient codes, clinical event data, clinical lab result data, order data, and others.

Furthermore, in some embodiments, various elements of the overall architecture 150 are designed to function optimally together. For example, aspects of each of various elements, such as the EMR/EHR systems 152, the other data sources 162, the HL7 messaging engine 154, the parser engine 156 and the analytics and presentation engine 158, and logic relating to each, may be designed to operate, communicate or interface quickly, efficiently or optimally with various of the other elements, as well as particular actual, possible, or anticipated clinical, medical, or health care related needs, requests or uses. Aspects of clinical, medical, or health care related needs, requests or uses can include, for instance, the analytic substance of the needed analytic results data (e.g., analytic results data relating to the probability of chest pain being associated with a heart-related event), medical end users and sites, end user or site electronic systems, and many other things. Furthermore, in some embodiments, the HL7 messaging engine 154 and the parser engine 156 design may take into account aspects of each other, as well as aspects of the EMR/EHR systems 152 (such as the formatting and structuring specifics of EMR data or HL7 messages coming from each of them), the other data sources, intermediaries, the design and structure of the analytics and presentation engine 158 and the EMR database 160 (including tables and views structures, for instance), particular actual, possible or anticipated clinical, medical, or health care related needs, requests or uses, and types of analytic results data.

In some embodiments, the design of the overall architecture 150 allows determination and presentation of needed analytic results data for particular clinical, medical, or health care related needs, requests or uses in real time or near real time relative to a time of entry of relevant current EMR data at EMR/EHR systems 152, or relative to a time of sending of the EMR data to the HL7 messaging system 154 or parser engine 156. In some embodiments, the relevant current EMR data can include the most current EMR data needed in determination of the needed analytic results data for a particular use case scenario, which can be used, in some cases, in addition to relevant historical EMR data. In some embodiments, relevant EMR data be determined in whole or in part by the analytics and presentation engine 158. It is to be noted that analytic results data can, in various embodiments, include any desired results data that results from analysis of EMR data.

In general, in various embodiments, various elements of operation of the inventive architecture 150 may operate or produce results faster than previously existing architectures. Such results can include determination and presentation of analytic results data, or other particular results or outcomes, such as parsing of an HL7 message by a parser engine to identify and extract needed or desired EMR data, for example.

In some embodiments, various forms of machine learning and machine learning models and feature sets may be used in various aspects of the architecture 150 and its operation. For example, machine learning may be utilized in building, updating or optimizing, such as periodically or continuously, the HL7 messaging engine 154 or its logic, the parser engine 156 or its logic, or the analytics and presentation engine 158 or its logic, which could include the EMR database 160 format and structure, including overall and individual table and view structures or designs, definitions and configurations, etc. In some embodiments, machine learning techniques are used in connection with current and historical EMR data stored, or other data, in the EMR database 160, potentially among other data.

In some embodiments, data received by, stored in, and potentially merged or integrated in the database 160, such as in tables and views, can include data from various sources. These sources are depicted generally as the EMR/EHR systems 152, as well as the other data sources 162 that can include any sources other than the EMR/EHR systems 152. Furthermore, it is to be understood that data from the EMR/EHR systems 152 and other data sources 162 may be received directly by the database 160, or may first pass through, and potentially be modified or transformed by, one or more intermediaries, such as various intermediary systems or entities. For example, in some cases, data from the EMR/EHR systems 152 may first pass through an intermediary billing-related entity.

Data received by the database 160 from the EMR/EHR systems 152 can include data obtained from HL7 message data or from non-HL7 data. In some embodiments, non-HL7 data does not pass through the HL7 messaging engine 154 or the parser engine 156, prior to being received by the database 160. In some embodiments, non-HL7 message data may be sent from the EMR/EHR systems 152 or the other data sources to EMR database 160 directly or after passing through and potentially being modified or transformed by intermediaries. For example, non-HL7 message data sent by the EMR/EHR systems 152, and not passing through the HL7 messaging engine 154 or the parser engine 156, may include non-real-time or non-near real-time, historical, batch, or periodically or intermittently sent data, where the period or frequency of sending or receipt, whether regular or irregular, can vary greatly. For example, the frequency might be a small fraction of second, one or more seconds, one or more minutes, one or more hours, one or more days, or even longer.

Other data, from the other data sources 162, can include non-public or public source data. The other data can include, for example, billing or insurance-related data. In some embodiments, the other data can include public data that may be used in connection with billing, insurance, health care or medical care providers, or other entities, parties, or aspects of medical or health care, or medical or health care data. For example, in some embodiments, public data may be used in connection with various stored data, such as for data enrichment or supplementation, or in connection with, or to confirm or verify, for example, registrations, licensing or name validation, in connection with providers, insurance companies, billing or billing companies, codes and coding, other parties or entities. For example, in some embodiments, data, such as codes or standards, may be obtained from public databases such as LOINC (Logical Observation Identifiers Names and Codes), or from sources associated with other standards or coding entities, such as National Provider Identifier Standard (NPI) data, for instance.

Figure 2:
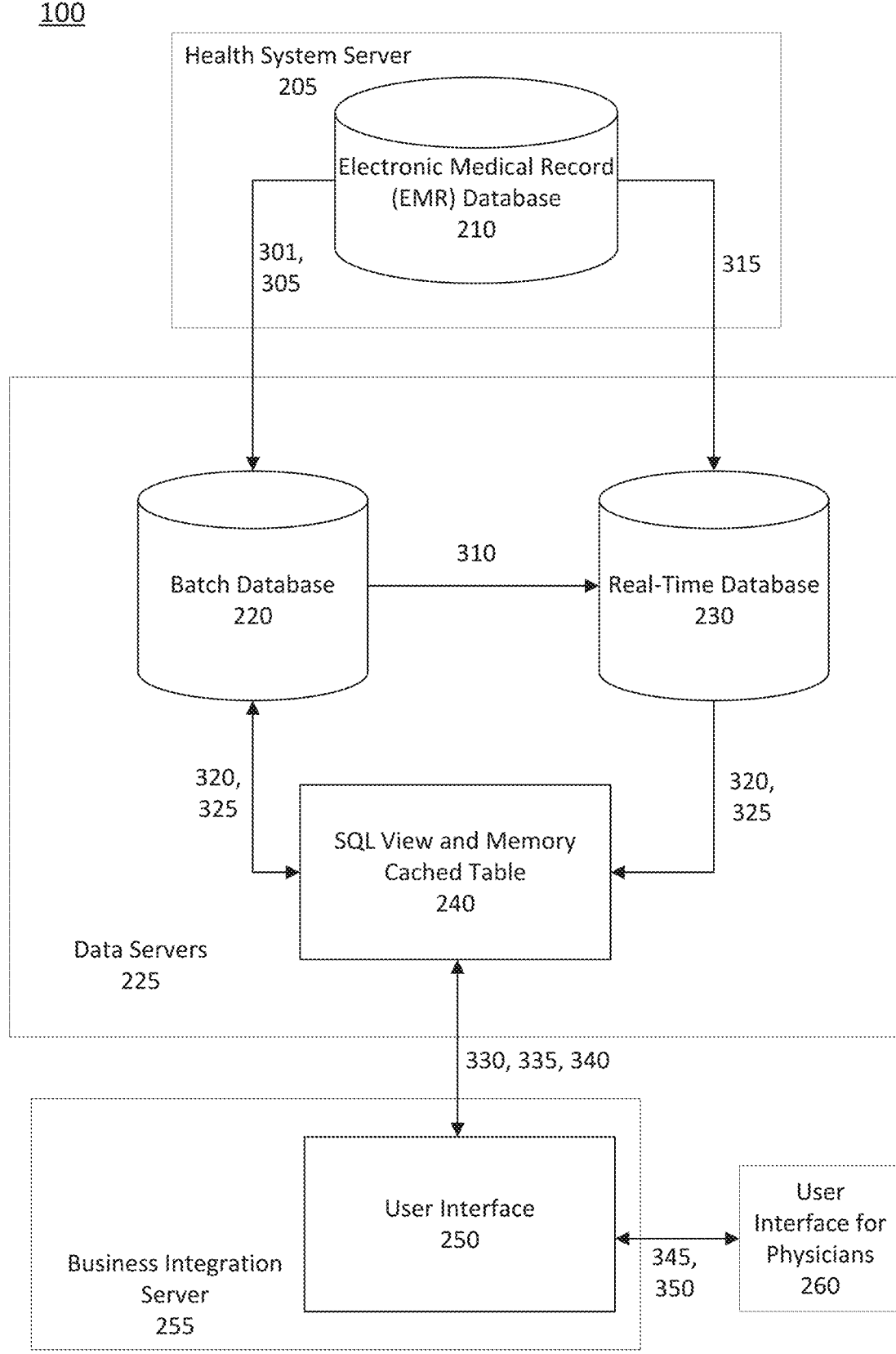
FIG. 2 illustrates a block diagram of the data flow and architecture of a system according to some embodiments of the invention.

FIG. 2 illustrates a block diagram of the data flow and architecture of a system 200 according to some embodiments of the invention. Depicted are one or more health system servers 210, one or more data servers 225, including a batch database 220, a real-time database 230, an SQL and Memory Cached Table 240. Data servers 225 are operably connected to Business Integration/Business Intelligence (BI) server 255 having a user interface server program 250, which is in turn operably connected to one or more exemplary user devices, each including a user interface for physicians 260. In various embodiments, elements such as the health system servers 210 and user devices 260, or portions thereof, may or may not themselves be part of the inventive system. For example, in some embodiments, the SQL and memory cached table 240 only, or operation thereof, or elements of the SQL and memory cached table 240, or elements of operation thereof, may constitute an entire inventive system, method, apparatus, architecture, data structure, computer readable media, etc.

It is to be understood that intermediary entities may be present in addition to those depicted, or multiple separate sub-entities of particular entities, and data may be received and sent from such non-depicted intermediaries or sub-entities to, from or within depicted entities. It is further to be understood that, while a single health system server 210, data server 225, SQL view and memory cached table 240, BI server 255, and user device 260 are depicted, each engine can be implemented by or using one or more networks, computers, servers, clients, applications, operating systems, software, hardware, etc., as well as various communications therebetween.

Health system servers 210 receiving and storing EMR data may be located at or associated with various sites, such as hospitals, medical facilities, doctor's offices, etc. EMR data may be entered, logged, recorded or input at such sites. For example, upon admission of a patient into a hospital, EMR data relating to the patient, e.g. patent's name, patient's demographics, billing information, insurance information, health-related complaint, lab tests ordered for diagnosis, collected vitals or other data, prescriptions, diagnoses, surgery history, and many other types of data, may be entered, recorded or logged, or collected and entered, recorded or logged, into the hospital's computerized EMR system. In addition, other types of EMR data may be entered.

EMIR data entered or logged into the health system servers 210 may immediately, such as in real time or near real time, be sent as a stream of data items directly, indirectly or via intermediary entities. Depending on specific circumstances, real time or near real time can be, for example, within seconds or a fraction of a second. In various embodiments, the EMR data sent from the health system servers 210 may be in various forms and formats, such as not yet formatted into HL7 messages, partially formatted into HL7 messages, or fully formatted into HL7 messages. EMR and other data present in health system servers 210 may be transmitted to data servers 225 and/or SQL view and memory cached table 240 where one or more machine learning models may operate on the EMR data to derive risk estimates for, e.g. acute coronary syndrome (ACS) or other medical conditions, diagnoses, or diseases for one or more patients.

In some embodiments of the present invention, criteria may be customized to identify patients at a high-risk for a 14-day emergency department (ED) revisit, and such patients may be among those retrieved by the callback tool for follow-up by an assigned physician or other clinician. In one embodiment of the present invention, a logistic regression model approach may be taken to identify patients at high risk for a 14-day revisit by calculating odds of returning. In another embodiment of the present invention, a decision tree model approach may be taken to identify patients at high risk for a 14-day revisit by determining "rules" for returning. Model features for evaluation could be based on, e.g., gender (one or more of, e.g., male/female/transgender/gender non-conforming), age group (e.g., 0-17, 18-25, 26-40, 41-64, 65+), number of ED visits in the last six months, zip code, reason for visit categories (e.g., alcohol-related disorders; chronic kidney disease; hemorrhage during pregnancy, abruptio placenta, placenta previa; immunizations and screening for infectious disease; open wounds of head, neck, trunk; other aftercare; other complications of birth, puerperium affecting management of mother; other disorders of stomach and duodenum; sickle cell anemia; skin and subcutaneous tissue infections).

In some embodiments, customized approaches, methods, techniques, measures, matrices, models, machine learning models, variables, algorithms, classifications, attributes may be used, for example, in high risk assessments. These may include, for example, machine learning techniques, logistic regression techniques, and/or decision tree techniques. For example, in some embodiments, techniques can be used in making predictions or determinations regarding the odds of a patient returning to an emergency department, or returning over some period of time, such as within 14 days, etc., which may, for example, be taken account in a high-risk assessment, determination or algorithm. In some embodiments, logistic regression techniques may be used in determining such odds, and decision tree techniques may be used in determining such rules, for example. In some embodiments, the type, quality and/or quantity of available or utilized data, or types of data, may be used to make determinations regarding the assessment itself, such as sensitivity, specificity, precision, accuracy, error, negative prediction value, prevalence, false positives, etc., which may be factored in to risk assessment determinations, for example. Furthermore, data regarding outcomes of predictions may be collected over time and utilized, for example, in assessing and refining the performance of high-risk assessment techniques, models, or algorithms themselves, such as, for example, by using such data as feedback for machine learning models, or model features, characteristics, training or refinement. In some embodiments, techniques including use of a confusion matrix, or visualization models, may be used in such performance evaluations, for example.

In some embodiments, various patient data and statistics, individual or group, may be utilized in high risk assessments and techniques. For example, in some embodiments, machine learning techniques may be utilized that use some portion of a set of patient group data as a training set, and some portion as test data, such as 75% training and 25% test, for instance. Categories of conditions may also be considered or utilized. For example, data regarding a certain number or proportion of patients in a particular category and the related disposition, or current status, may be required or utilized. In some embodiments, for example, data is utilized to determine categories more or most likely to result in emergency department revisits may be utilized and factored into high risk assessments. For example, in some embodiments, categories may include, for example, alcohol-related disorders, chronic kidney disease, hemorrhage during pregnancy, abruptio placenta, placenta previa, immunizations and screening for infectious disease, open wounds of head, neck, trunk, other aftercare, other complications of birth, puerperium affecting management of mother, other disorders of stomach and duodenum, sickle cell anemia, skin and subcutaneous tissue infections, or others.

In some embodiments, other patient(s) data and category data may also be utilized and factored in, such age or other demographic, medically relating or not medically related, patient or patient category or characteristic data, such an age or age group, zip code or gender, for example.

In some embodiments, real-time, HL7 data is used to create patient lists that can be used with great flexibility, specifically in this case, to attribute patients or identify high-risk patients in real-time.

Similarly, in the callback tool, the BI server 155 compiles incoming query requests from users (e.g. ED physicians and other clinicians) via a user interface client running on user device 160 and translates the data to SQL or other readable query format and sends the request to back-end databases at data servers 125 and modeling servers 130. BI server 155 will also receive the query results and prepare the data results for display on the user interface running on user device 160.

Health system server 105 includes one or more EMR databases 110. Health system server 105 is connected to one or more data servers 125. In various embodiments of the invention as discussed above, one or more data and model servers 125 comprise a batch database 120 and real-time database 130. Batch database 120 may be operably connected to health system server 105 and may receive batch data at pre-specified time intervals from EMR database 110 via network connection 201 and 205. In various embodiments of the invention, real-time database 130 may also be operably connected to health system 105 and may receive data in real-time or near real-time upon user request via network connection 215. Batch database 120 may also be operably connected to SQL view and memory cached table 140 via network data connections 220 and 225, and to real-time database 130 via network data connections 220 and 225. Real-time database 130 is also connected batch database 120 via network data connection 210. SQL view and memory cached table 140 is also operably connected to BI server 155 running user interface server program 150 via network data connection 230, 235 and 240. BI server 155, via user interface server 150, is also operably connected to the user interface running on user device 160 through network connections 245 and 250.

Figure 3:
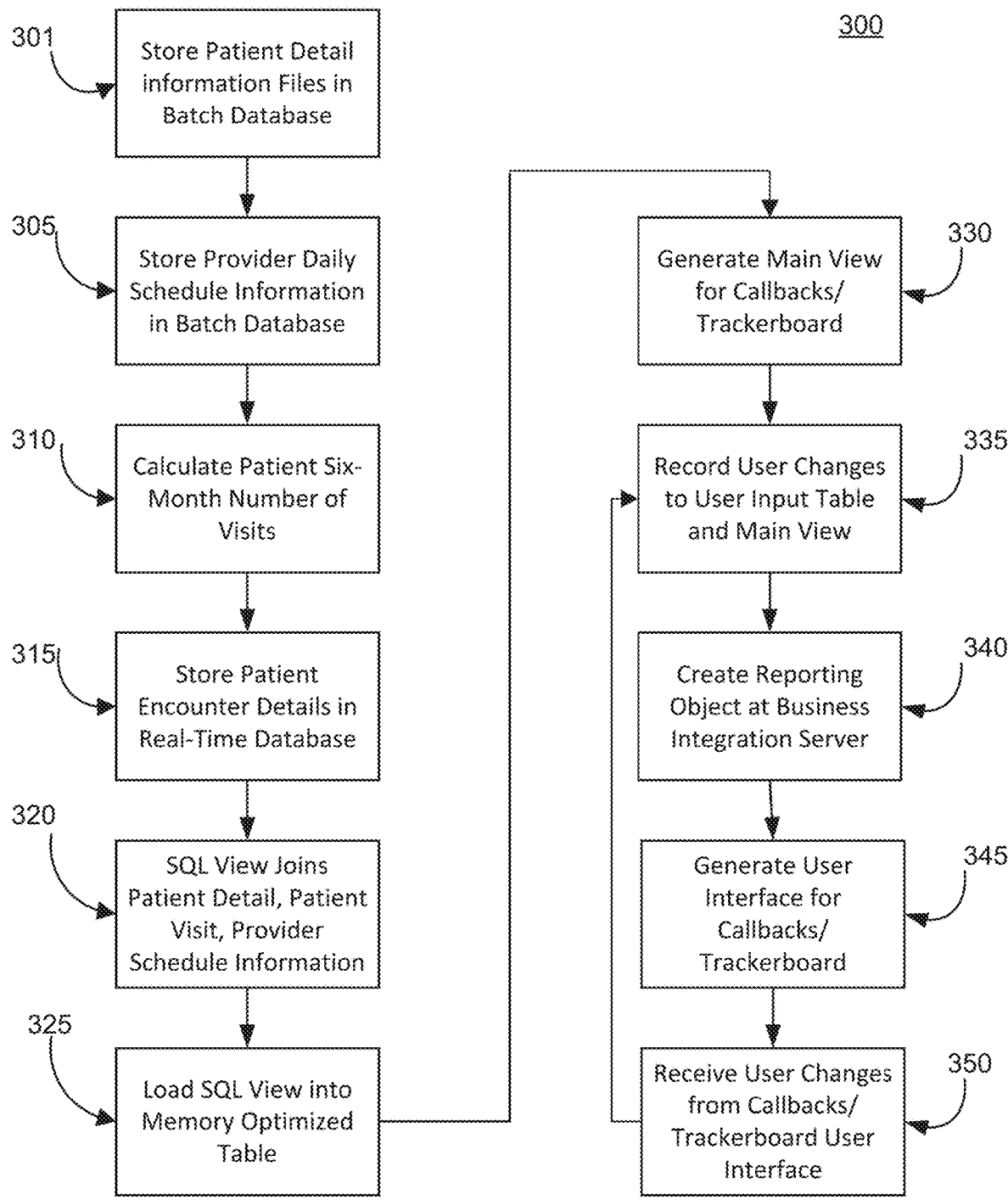
FIG. 3 illustrates a flow diagram of a method according to some embodiments of the invention.

FIG. 3 illustrates a flow diagram of a method according to some embodiments of the invention and describes the data flows that were shown in FIG. 1 as network connections. In step 301, daily batch data feeds for patient records are retrieved from EMR database 110 and stored in the batch database 120. In step 305, provider daily schedule information is stored in the batch database 120. In step 310, patient detail information stored in the batch database 120 is used to calculate patient six-month number of visits. In step 315, streaming HL7 messages relevant to patient encounter details are stored in real-time database 130. In steps 320 and 325, the daily batch data feeds from batch database 120 including patient detail information and provider daily schedule information, the patient encounter details and provider daily schedule information in real-time database 130, and patient six-month visit information are passed to SQL view and memory optimized table 140. In step 330, the main SQL views for the callbacks/trackerboard tools are generated. In step 335, user changes to the main view for the callbacks/trackerboard tools may be recorded, as well as user changes to the user input table. In step 340, a reporting object is created at BI server 155. In step 345, the user interface for the callbacks and/or trackerboard tools is generated at user interface server program 155 and may be displayed on a user interface client of clinician user device 160. From time to time, user interface client of clinician user device 160 may also receive updates and changes to the patient and provider data shown in the client user interface, which is then updated in step 335.

Figure 4:
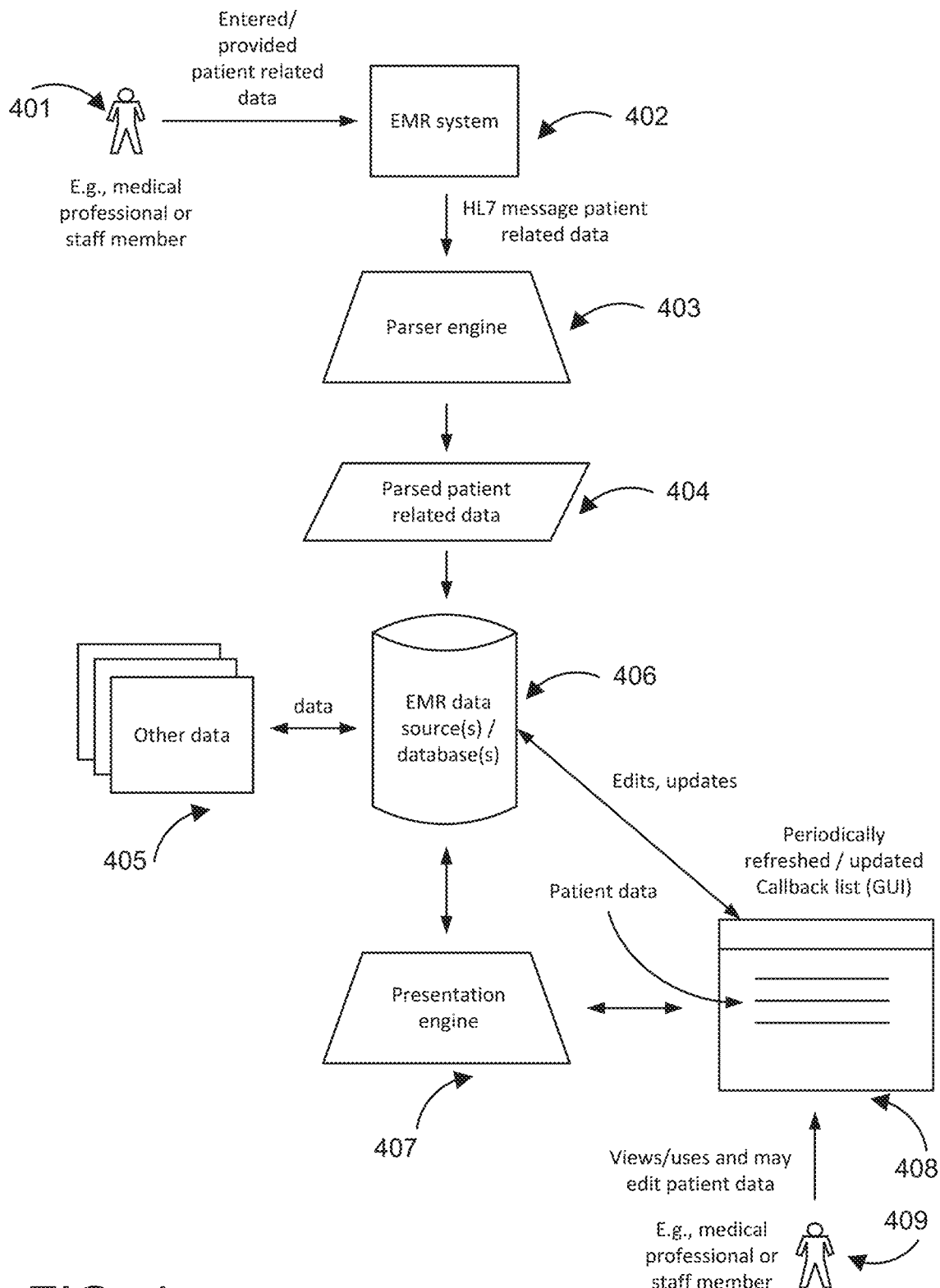
FIG. 4 illustrates a block diagram according to some embodiments of the invention.

FIG. 4 illustrates a block diagram according to some embodiments of the invention, including a parser engine 403 and a presentation engine 407. As depicted, a person 401, such as a medical professional, staff member, or a scribe, enters or otherwise provides patient related data into an EMR system 402. HL7 message data, including patient related data, is sent to a parser engine 403 (as further described in co-pending U.S. patent application Ser. No. 16/297,456, filed on Mar. 8, 2019, which has been incorporated by reference in its entirety). The parser engine parses the HL7 message data 404 and sends the parsed patient-related data to an EMR data source(s) or database(s) 406. In addition to the parsed data, other data 405 including patient-related data from other data sources, such as may include historical patient related data, insurance or billing related data, etc., is sent to and stored in the EMR data source(s) or database(s) 406.

A presentation engine 407 collects data from the EMR data source(s) or database(s) 406, including parsed and other patient-related data, and uses the collected data to generate periodically updated callbacks data and a periodically updated GUI-based callback list 408 made available or presented to a user 409, such as a medical professional, staff member or scribe. In some embodiments, the user 409 may update some of the information displayed on the callback list 408, and the edits are sent to, and used to update, the EMR data source(s) or database(s) accordingly. In some embodiments of the present invention, access is controlled centrally through a single sign-on (SSO) process. Users may access the callback tool suite through client devices such as hospital computers, personal computers, or personal mobile devices. Users may include clinicians, other health care providers, and hospital staff. In one embodiment of the present invention, two separate platforms may be leveraged to provide an SSO experience to users. For example, Okta may be used for the desktop platform while Usher may be used for the mobile platform. In some embodiments of the present invention, the call back tool suite follows a Secure Development Lifecycle and its security program is based on NIST standards.

Like the callback tool, the trackerboard tool uses real-time (HL7) data so that providers can "add" patients to their specific list. The trackerboard tool provides a running list of all patients as they enter the hospital and then allows the provider or designee (e.g., scribes) to assign a patient to their list using a drop-down field. Other patent applications describe exemplary embodiments of this trackerboard tool in detail, including, but not limited to, co-pending U.S. patent application Ser. No. 16/378,439, filed on Apr. 8, 2019, which is herein incorporated by reference in its entirety. In some embodiments of the present invention, the callback application tool is provisioned to providers (physicians, advanced providers), scribes, and on-site administrators (aka Practice Administrators or Program Managers).

In some embodiments, the trackerboard and callback tools provide capabilities to assign to care navigators, identify patients that came in from certain SNF partners, identify common diagnoses that could be managed in an outpatient setting, etc. In some embodiments, user input to modify, update, enter or overwrite data displayed on the trackerboard or callback tool can be written back directly to the original source of the data, or written back to an intermediary source of the data and later written back to the EMR system and database. In some embodiments, once the HL7 real-time data as well as user input data matures, it gets written back to the main EMR system.

In some embodiments, the trackerboard tool takes real-time, HL7 admission, discharge, and transfer (ADT) data sent from hospitals and displays them in near (within seconds) real-time in a dashboard. In some embodiments, the trackerboard tool filters patients by ADT status, where the data field indicating discharge is null. The dashboard is typically provisioned to emergency department providers and scribes at the site but can be provisioned to others who need/are allowed access to this data and can be accessed at non-hospital locations, i.e., you do not have to be on hospital premised to view the data. The trackerboard, like the callback tool, displays patient data (Patient MRN, encounter number, admit date/time stamp, insurance/payer, number of previous emergency department visits) as patients arrive in the hospital emergency department.

In some embodiments, the trackerboard patient list may be run through a High-Risk algorithm that can be customized per hospital site. These "high-risk" patients or patients with additional diagnoses or payer groups, etc. can be customized on the trackerboard patient list to identify patients in real-time based on a variety of demographic, revisit, or patient-specific characteristics. These "high-risk" patients may be highlighted based on risk and may be visually distinctive by formatting such as font, color, or a visible marker, quickly visually identifying existence of risk or the type of risk. These "high-risk" patients on the trackerboard patient list may be highlighted also on the callback tool and interface as further discussed herein.

In some embodiments, there is an additional column that allows providers or scribes to "attribute" a patient case to a certain provider for callbacks purposes. The reason for this is that the ADT data sent from hospitals is generally completed by hospital registration staff, without much concern for accuracy in terms of providers who saw the patient. The last column in the trackerboard patient list allows users to "re-assign" patient case so that the case is accurately reflected in the provider-specific patient list for callbacks. The tool does not write back in to the EMR. Write-back fields are captured in our SQL database and the business intelligence platform exposes the values written back.

In some embodiments, the trackerboard patient list provides reporting or analytics or real-time information to insurance companies by identifying patients by insurance status in real-time at the point of clinical intervention. For example, if an insurance company wants to test an intervention on COPD patients who utilize the emergency department, the trackerboard identifies those patients for the scribes to conduct an intervention. In some embodiments, the trackerboard patient list provides federally qualified health centers (FQHC) who want their clinic-enrolled patients to know about appropriate outpatient services. The trackerboard patient list may identify patients whose payers are at the FHQC.

In some embodiments, the trackerboard uses EMR extracts combined with data from HL7 feeds to create a real-time historical view of patients for a particular site. Using this history in real-time, the trackerboard can analyze the data and create predictions of key metrics such that decision makers can address management needs more rapidly.

Emergency Departments typically track patient lists by keeping a running list of new patients that come in through the emergency department, where providers, beds, and nurses are assigned. However, the conventional way of keeping a running list of patients is problematic in that it merely displays data from an EMR system and database, the EMR system and database is resource heavy to access, nearly impossible to access, display or modify in real-time, in part because the data is typically batch stored in the EMR database, and the data in the EMR system and database is restricted and sometimes not yet stored, available and permitted to be corrected or changed. Conventional systems provide patient lists that are only available within the hospital site on EMR-owned patient lists and there was limited write-back functionality to those, i.e., nurse and provider assignments, bed assignments.

In some embodiments, the trackerboard tool is EMR-agnostic, meaning that it can take HL7 data from any EMR system and display the data for scribes and providers. Thus, there is no need to license a particular EMR system in order to provide this data in real-time thus, the tool is low cost, low maintenance, low resource and scalable to any site using any system or platform. The trackerboard and callback tools also allows scribes and providers to write-back into the tool to flag patients who are high-risk or who should be followed up by case management or care navigators.

FIG. 5 illustrates a screenshot of a trackerboard exemplary user interface display according to some embodiments of the invention. The trackerboard is used to derive the list of patients to populate the callback application for the physician/clinician to call back after their day's shift ends. The user interface dashboard 500 for the trackerboard is generally designed to be available to clinicians in the ED, and in some embodiments of the present invention, comprise a table having rows and columns, where each row corresponds to one patient in the ED. The user interface dashboard 500 is updated in real time or near real time. In some embodiments, a record is created for all ED patients regardless of disposition. That is, user interface dashboard 500 shows all ED encounters as they arrive in the ED and disposition has not been made on these patients, as it will show patients who will eventually be discharged or possibly admitted. In some embodiments, each row corresponds to one patient record including patients that were seen up to 12 hours from ED arrival time 550. In some embodiments, after 12 hours, the patient will be removed from the list.

The user interface dashboard 500 may display filtered results based on selected sites 510, which may be a field configured as a drop down allowing to filter the patients by their location, including for example the location of the ED. In some embodiments, a site must be selected before entering data user interface dashboard 500 and if the site is empty, then the information may not be properly saved. The patient name 520 column includes a customizable field displaying at least a patient's first and last name. In some embodiments, the patient name 520 field may also include the patients age, in parenthesis, after the name. The MRN 530 column includes a medical record number for patients and encounters. The encounter number 540 column includes an identifier for a patient encounter. In some embodiments, the encounter number 540 is numeric or alphanumeric and may be randomly or serially generated or queried from a database. The ED arrival time 550 column includes the patient's arrival date and/or time into the ED. The ED visits in 6 months 560 column includes a count of ED visits for the patient in the last 6 months. The last ED visit 570 column includes the last date and/or time the patient visited the ED. In some embodiments, the date and time related fields include automated time stamps. The attending provider 580 column includes the name of a provider recently or currently assigned to the patient. The provider edit icon 590 allows you to update the provider information for all patients.

In some embodiments, there may be additional fields and settings such as override and hybrid fields or settings (not illustrated). When activating the override setting, this setting will completely ignore the HL7 feed and will require overrides from the user interface dashboard 500, including for example attributing patients to a provider. When activating the hybrid setting, this setting will leverage the HL7 messages as is but also accept overrides from the user interface dashboard 500. Attribution will default to HL7 unless an override is completed. In some embodiments, there may be additional fields related to health risks (not illustrated). For example, for patients presenting in the ED with unspecified chest pain may have a cardiac predictive risk estimate and predicted outcome displayed in an additional field or column, for example, as a check box. In some embodiments, the user interface dashboard 500 refreshes periodically, for example, every five minutes. In some embodiments, there may be a submit button which may appear upon making entries or changes into and be used for updating the user interface dashboard 500. In some embodiments, unsubmitted information may be lost in the case of a refresh. Other patent applications describe exemplary embodiments of this user interface display in detail, including, but not limited to, co-pending U.S. patent application Ser. No. 16/378,460 filed on Apr. 8, 2019, which is herein incorporated by reference in its entirety.

Figure 6:
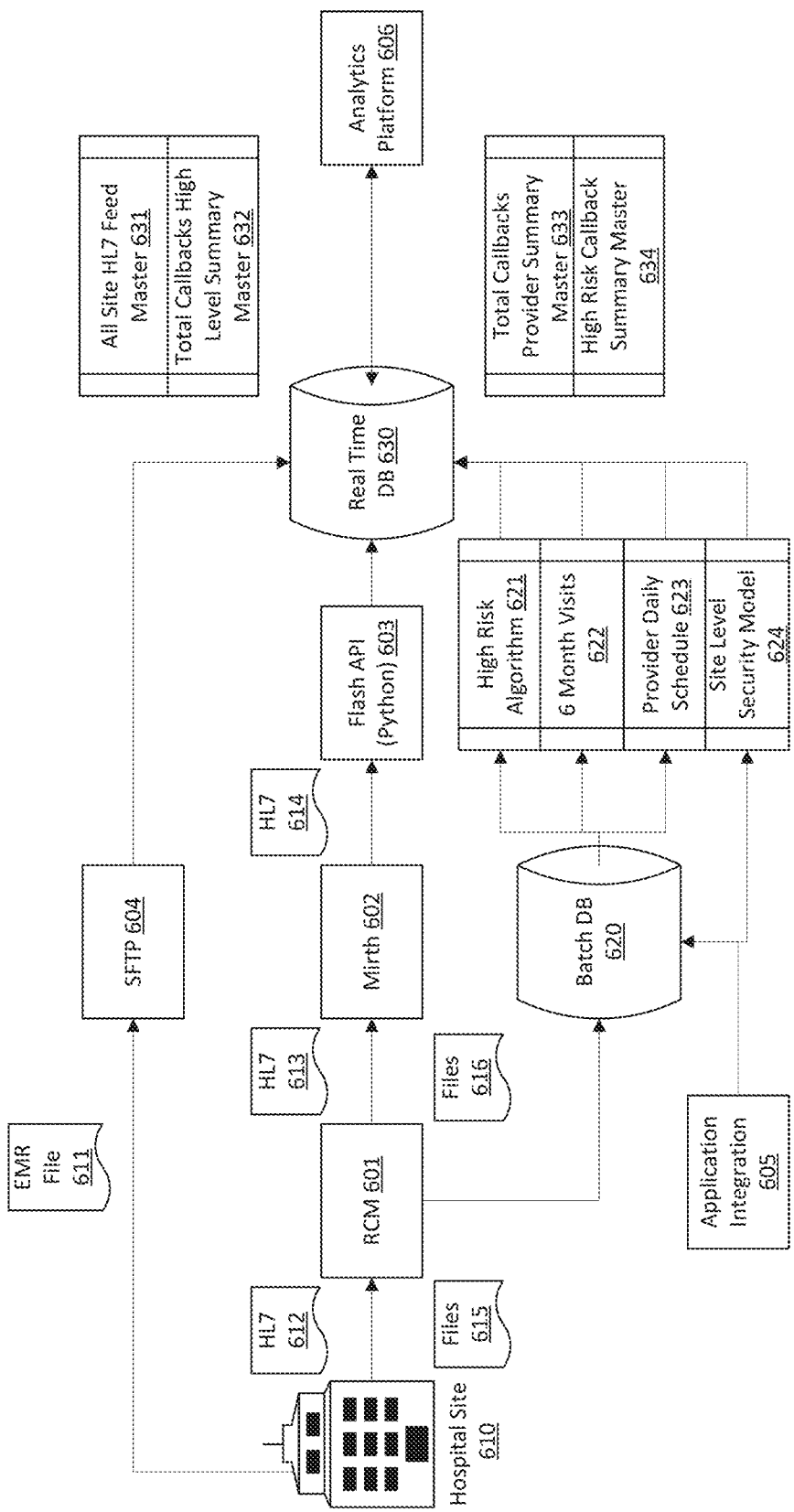
FIG. 6 illustrates a block diagram of the data flow and architecture of a system according to some embodiments of the invention.

FIG. 6 illustrates a block diagram of the data flow and architecture of a trackerboard and callback system according to some embodiments of the invention. Scribes, physicians or nurse practitioners log healthcare encounter events into EMR systems at Hospital Site 610, including for example, patient demographics and lab tests. Hospital Site 610 transmits patient detail files, including HL7 612 and Files 614 to a data engineering team at Revenue Cycle Management (RCM) 601 for processing. The HL7 612 file may include raw HL7 stream data generated by the EMR system. In some embodiments of the invention, the HL7 612 and Files 614 may be transmitted via a secure VPN. Data from HL7 612 and Files 614 may be used for any number of purposes as approved by the hospital or health care facility, including billing purposes, as well as populating information into the Callback and trackerboard tools. The files may document which patients have been diagnosed with conditions for disease management. The HL7 612 file may include real time data that is transferred via HL7 messages from the Hospital Site 610. Specifically, the tool uses the following data fields: Patient Name, Discharge Date, Medical Record Number (MRN), Encounter Number, Payer Type, Contact Phone, Reason for Visit, Age, DOB, Diagnosis (For High Risk/Disease Management).

The files are then sent as HL7 613 to Mirth 602 for further processing. Mirth 602 may include a server for processing HL7 messages. Mirth 602 server sends the HL7 614 file data as re-serialized in HTTP Body payload. Once the file HL7 data 614 leaves the Mirth server, it proceeds to Flash API (Python) 603, which may be an API and a python application. In some embodiments, Mirth 602 may include an open source tool that implements MLLP protocol which formats HL7 messages and gives it a structure. In some embodiments, Mirth 602 recognizes when a HL7 message starts and stops. In some embodiments, Mirth 602 ingests data from upstream hospitals and serves as input to the Flash API (Python) 603. In some embodiments, Flash API (Python) 603 uniquely identifies different segments present in a single HL7 message and parses data based on locations predefined by HL7 specification along with custom locations supported by the site.

The Files 615 are sent to Batch DB 620. In some embodiments, Batch DB 620 may include Provider Daily Schedule 623, and 6 Month Visits 622 which may include ED visits for the past six months, Site Level Security Model 624, and High-Risk Algorithm 621. Provider Daily Schedule 623 is scheduling information that documents each provider's shifts, when they work, how long they work, respective facilities, and the like. This information may be summarized to calculate the number of shifts each provider at each site has per month. In some embodiments, schedule information is summarized to calculate the number of shifts each provider at each site has per month. In some embodiments, Site Level Security Model 624 includes row level security which restricts data access based on a user's credentialed sites or locations and roles at those respective sites or locations. Access is maintained and audited by a centralized security administration team which is responsible for provisioning, reviewing, and terminating access to applications.

In some embodiments, Batch DB 620 may include a billing database, historical data, data received from revenue cycle management entities, data loaded in batches, for example, once a month, including data for multiple, for example hundreds of sites.

EMR File 611 is data from the Hospital Site 610 that is sent via the SFTP 604 protocol to the Real Time DB 630 database. In some embodiments, EMR File 611 includes a direct load of a flat file provided by the hospital from their EMR system to enrich existing data for use in disease management. For example, the list of diagnosis codes to flag patients with specific diseases are hospital specific and allows for maximum flexibility.

The Real Time DB 630 database includes EMR data (e.g., EMR File 611), historical data (e.g., from Batch DB 620) and HL7 real-time data (e.g., HL7 612, HL7 613, HL7 614) and provides various views or datasets such as All Site HL7 Feed Master 631 (the main source for trackerboard), Total Callbacks High Level Summary Master 632, Total Callbacks Provider Summary Master 633, and High Risk Callback Summary Master 634. In some embodiments, All Site HL7 Feed Master 631 joins real time HL7 data and batch DB, and historical data to provide a real time patient list of patients currently in the ED. The Analytics Platform 606 may use the data in Real Time DB 630 for presentation. The Analytics Platform 606 and the Real Time DB 630 may have a bi-directional connection. In some embodiments, the Analytics Platform 606 may write back data or override data to Real Time DB 630, for example, when a user enters provider attribution via an interface. The Analytics Platform 606 may provide a customizable patient list for patients currently in the ED, including details about their visit history, high risk determination, and diagnosis. In some embodiments of the present invention, Batch DB 620, Real Time DB 630, and Analytics Platform 606 may be co-located in a SOC2 certified data center and follow standard at-rest and in-transit encryption protocols.

The user interface dashboard 400 and the trackerboard tool data flow and architecture 600 allows for patient information processing acceleration techniques to improve system performance, reduce performance variability, increase capacity and throughput, while also preferably reducing the physical and power requirement footprint and lowering the cost of implementation. The user interface dashboard 400 and the trackerboard tool data flow and architecture 600 overcomes the constraints of traditional computing concepts associated with EMR-owned patient lists related to limited write-back functionality, moving data from one server to another, or moving data between physical components within a single server, or between different applications or processes within a single server. Such traditional computing concepts can introduce capacity and performance constraints, which may be partially or wholly overcome by utilizing the EMR-agnostic trackerboard tool which can take HL7 data from any EMR system and display the records for scribes and providers, as described herein in the context of the various embodiments.

Application Integration 605 refers to internal system application integration used in some embodiments of the invention, integrating internal data sets containing user information (name, NPI, exchange directory name, hospital site affiliation), provider scheduling, and other enterprise data with the internal system applications. In some embodiments of the invention, these internal data sources may range from enterprise applications such as SalesForce to health care facility patient and provider scheduling platforms. Internal data for application integration may be received in a batch process and leveraged for developing user security, provider analytics for shifts worked and calculating their benchmarks based on threshold X number of shifts worked. In one embodiment of the invention, a default goal for the application is 2 callbacks per provider per shift of work. In some embodiments of the invention, the default goal can be customized by medical administrators or directors using a configuration panel for the tool suite.

The user interface dashboard 400 and the trackerboard tool allows for patient information processing acceleration techniques to improve system performance, reduce performance variability, increase capacity and throughput, while also preferably reducing the physical and power requirement footprint and lowering the cost of implementation. The user interface dashboard 400 and the trackerboard tool overcomes the constraints of traditional computing concepts associated with EMR-owned patient lists related to limited write-back functionality, moving data from one server to another, or moving data between physical components within a single server, or between different applications or processes within a single server. Such traditional computing concepts can introduce capacity and performance constraints, which may be partially or wholly overcome by utilizing the EMR-agnostic trackerboard tool which can take HL7 data from any EMR system and display the records for scribes and providers, as described herein in the context of the various embodiments.

By way of non-limiting example, the systems and methods of the various embodiments of the invention described herein reduce the processing duplication that occurs in traditional electronic patient information management infrastructure and reflect a departure from the traditional paradigm of standardized EMR-based processing. The trackerboard tool and user interface dashboard 400 reduces the number of processing steps, including the need for traditional EMR processing mechanisms. The trackerboard tool and user interface dashboard 400 also reduces the duplicative nature of entering and querying patient information records and a variety of other processing steps.

Both the callback and the trackerboard user interfaces 400 are constructed using analytics platform 606. In some embodiments of the present invention, the callback application tool consists of a desktop and mobile version. Both desktop and mobile versions of the callback application tool present provider-specific patient lists, containing patient name, date of service, insurance, any risk status (e.g., multiple ED visits over last 6 months), phone number, and drop-down fields indicating status of callbacks (i.e., spoke to patient, no answer/left message, etc.). The tool has two modes of populating the patient list: real-time data (HL7) or through manual entry. With real-time data, programming logic pulls data directly from databases to pre-populate provider-specific lists. With the manual entry mode, providers or designees (e.g., scribes) enter in patient information into the callback entry form that then pulls that information into provider-specific lists. The tool logs completed callbacks and also provides summary statistics on completed callbacks over time. The mobile version has the same functionality as the desktop version but has the added functionality of allowing providers to make phone calls directly from their cell phones. The mobile versions with automated dialing applications that mask the user's outgoing mobile phone numbers with a pre-specified general phone number, e.g. Doximity dialer, so that the phone number shown at the recipient's phone could be displayed as the hospital switchboard/operator/answering service.

In one embodiment of the present invention, the callback application tool is built leveraging the MicroStrategy business intelligence platform and multiple layers of security. In one embodiment of the invention, users are provisioned access to the desktop platform via the Okta application. The tool suite is further secured at the application integration (e.g., MicroStrategy) layer, restricting user access to tools for which they have been provisioned to and which are relevant to their workflows. In some embodiments of the present invention, the callback application tool has row level security in place which restricts data access based on a user's credentialed sites/locations and roles at those respective sites/locations. In some embodiments of the present invention, access is maintained & audited by a centralized security administration team which is responsible for provisioning, reviewing, and terminating access to the callback application.

In one embodiment of the present invention, the callback mobile application is also built on a business intelligence platform such as the MicroStrategy platform and is compatible with both Android & iOS devices. Users are then provisioned to the mobile application by a centralized security administration team via an Okta group. Provisioning into this master security group then prompts the centralized security administration team (such as Usher Security Network) to issue an electronic badge to the user—allowing users to access the mobile applications via standard mobile authentication methods (i.e. pin codes, biometrics, etc.).

Figure 7:
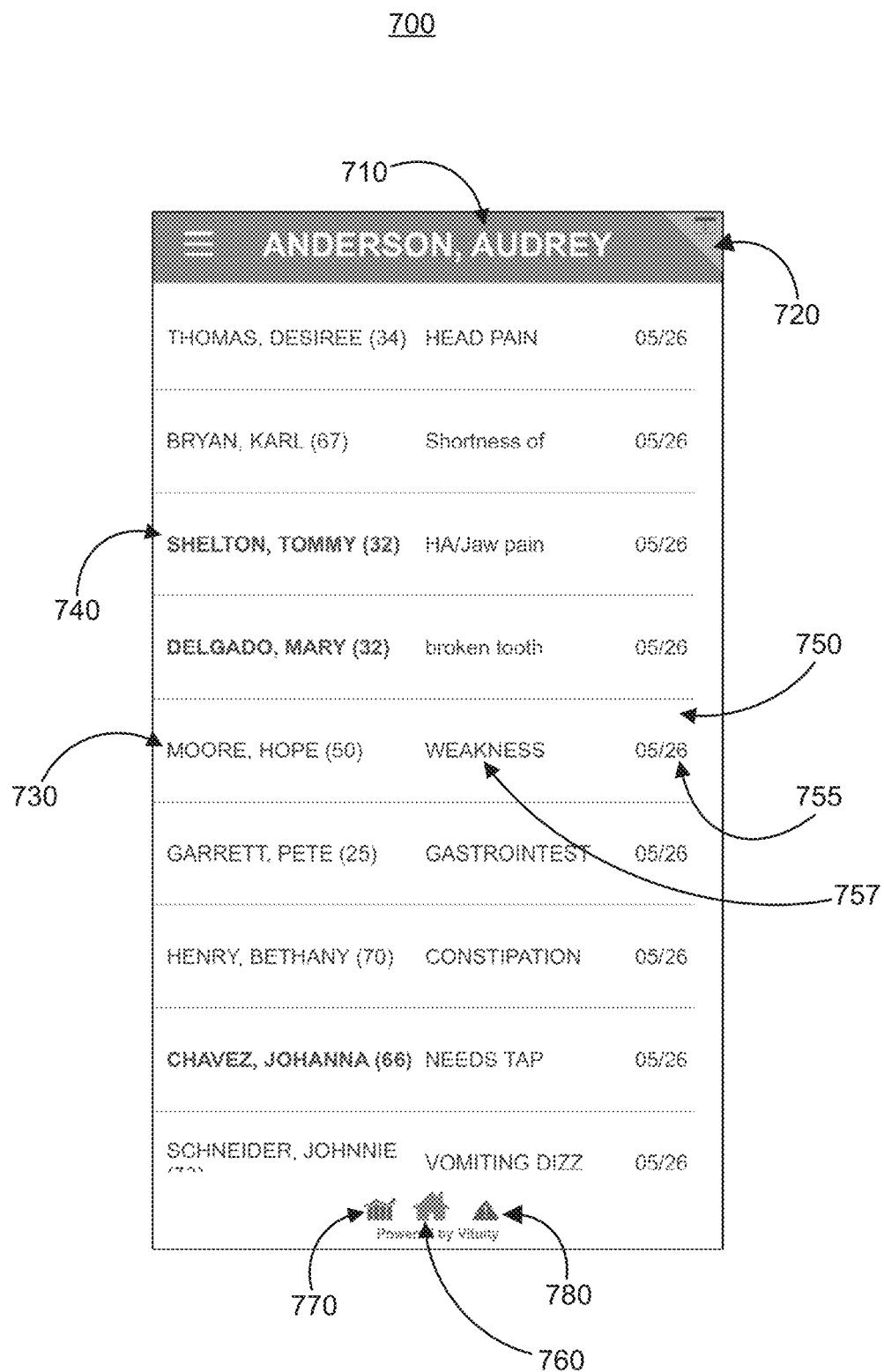
FIG. 7 illustrates a screenshot of an exemplary user interface display according to some embodiments of the invention.

FIG. 7 illustrates a screenshot of an exemplary user interface display according to some embodiments of the invention. Callback tool main interface 700 shows an exemplary home page including a main menu and patient callback list that may be displayed on a client device (i.e., a smart phone) belonging to a user such as a physician or other clinician. As mentioned above, each patient callback list is specific to the physician/clinician, and so the title bar 710 of the callback tool interface 700 shows the physician/clinician's name (in the example here, the name is shown as Audrey Anderson). The physician/clinician may work at multiple health care facility sites. As each patient callback list is also specific to a particular health care facility site, a site selection dropdown menu 720 may be used by the physician/clinician to select a health care facility site.

Figure 7A:
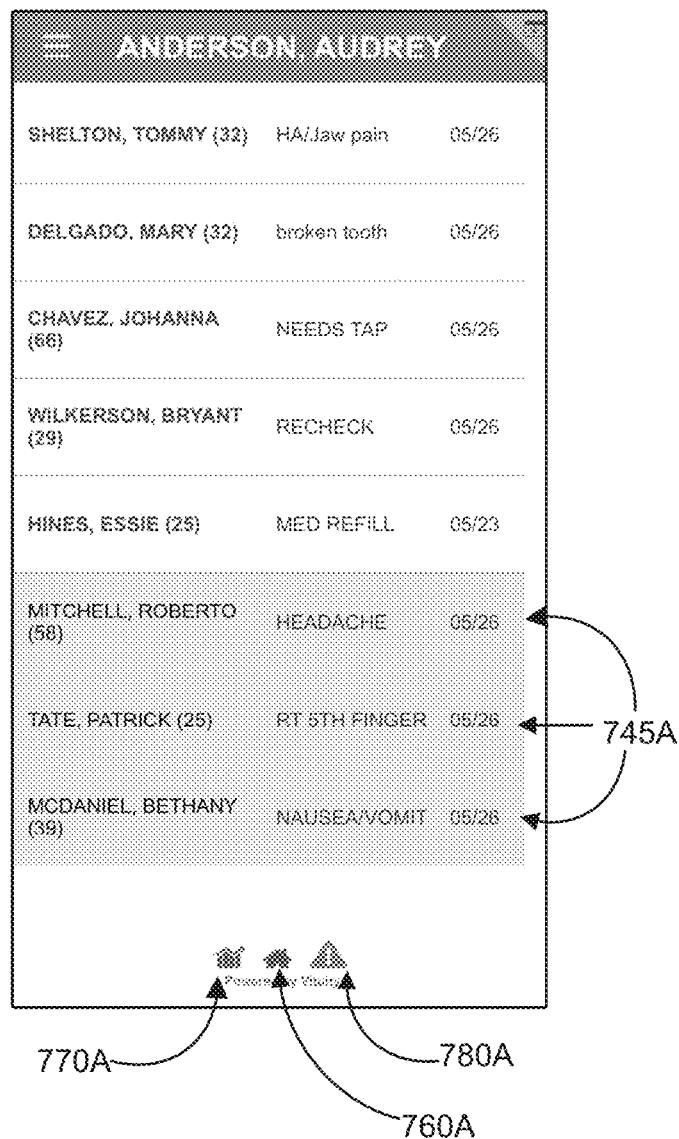
FIG. 7A illustrates a screenshot of an exemplary user interface display for prioritizing high-risk patient callbacks according to some embodiments of the invention.
Figure 7B:
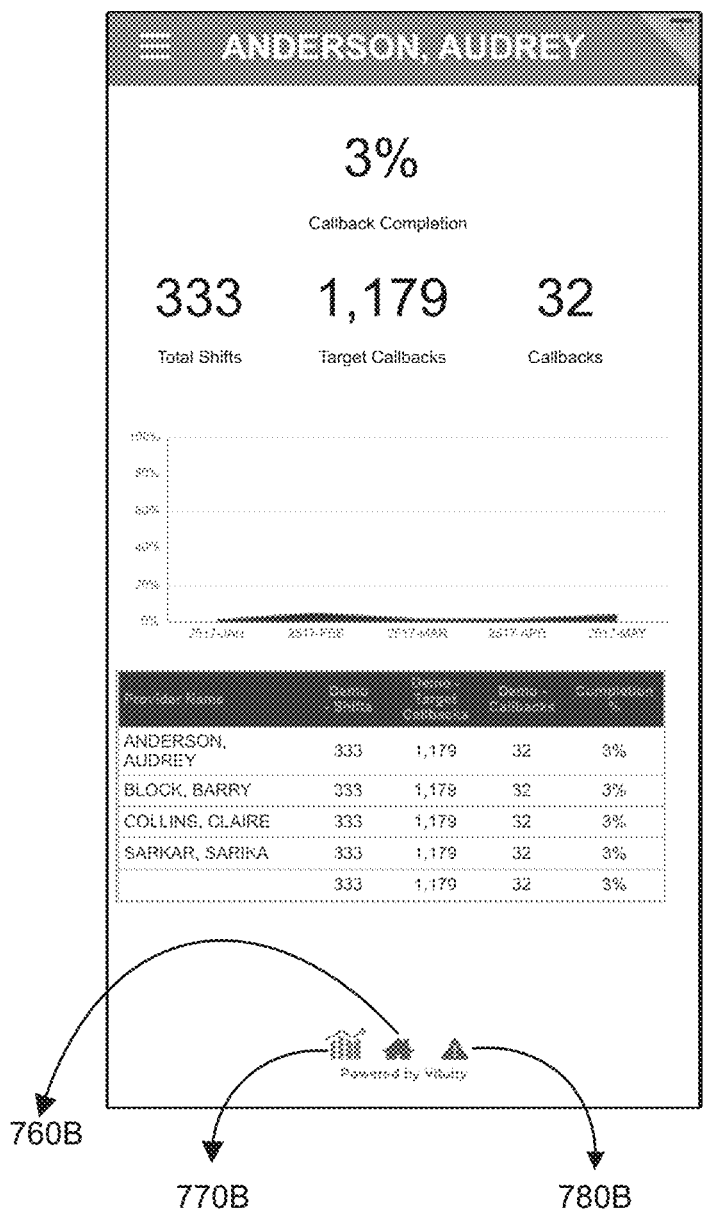
FIG. 7B illustrates a screenshot of an exemplary user interface display showing an administrative view according to some embodiments of the invention.

Below the site selection dropdown menu 720, a patient callback list with each patient represented as a line entry, for example patient line entry 750. Patient line entry 750 includes a patient name selected for follow-up 730, which may be highlighted for high-risk patients (as shown in example 740). The patient name 730 or 740 includes a customizable field displaying at least a patient's first and last name. In some embodiments, the patient name field 730 or 740 may also include the patients age, in parenthesis, after the name. Patient line entry 750 also includes a date of discharge 757, and diagnosis 755 for each patient. Along the lower border of interface 700 is a home button 760, high risk callback list button 780 so that the physician/clinician user may view a list where only the high risk patients are shown or the high risk patients are listed first, in order to prioritize the high risk patients for callback, as shown in screenshot 700A in FIG. 7A; and an analytics button 770 which will display callback tool analytics/statistics for the physician/clinician user (or site-specific analytics/statistics for users with administrator/manager privileges) as shown in screenshot 700B in FIG. 7B. In some embodiments of the invention, completed callbacks may be shaded in gray or otherwise highlighted as shown in 745A of FIG. 7A. Buttons 760, 770, and 780 (and 760A, 760B, 770A, 770B, and 780A, 780B similarly in FIGS. 7A and 7B respectively) may be activated, when displayed on a touch screen, by any of a variety of methods, including touch (i.e., finger press), or using a directional swiping or sweeping motion across the screen (e.g., swipe left to view analytics, and swipe right to view the high-risk patient callback list).

FIG. 8 illustrates another screenshot of an exemplary user interface display according to some embodiments of the invention. Patient detail interface 800 is displayed on a client device (i.e., a smart phone) belonging to a user such as a physician or other clinician once they have selected a specific patient in the callback tool main interface 800 to call. The patient name title bar 810 includes a customizable field displaying at least a patient's first and last name. In some embodiments, the patient name title bar 810 may also include the patients age, in parenthesis, after the name. Patient detail box 820 displays additional details about the patient that may be pertinent for the physician/clinician to refer to during the call, such as discharge date, discharge time, patient medical record number, patient encounter number, insurance payer/status, diagnosis/reason for visit, patient phone number, etc. The physician/clinician may call the patient directly by touching/activating the call button 825, which may activate the smart phone's telephone dialing function (and display the originating phone number on the patient's caller ID which may not be desired by the physician/clinician). Alternatively, phone number masking activation button 830 may be touched/activated to call the patient directly using a calling application with a masking function (such as Doximity dialer) and without displaying the originating phone number on the patient's caller ID. Instead, the calling application may mask the originating phone number by displaying a pre-specified phone number (such as the hospital main number or ED main number) on the patient's phone/mobile device's caller ID.

Provider update area 880 includes callback outcome dropdown menu 840, patient status dropdown menu 850, and an editable comment field 860. In some embodiments of the present invention, callback outcome dropdown menu 840 may require the user to specify the results of the callback by selecting between options such as for example, "No Answer", "No Answer, Left Message", "Spoke to Patient", "Spoke to Family Member", "Wrong Number", "Did Not Call", and "Other". In patient status dropdown menu 850, the physician/clinician may be required to specify the current status of the patient at the time of the call; for example, "Patient Is Well—No Further Follow Up Needed", "Patient Is Instructed—See Comments", "Patient Is Currently Admitted", and "Not Applicable". The physician/clinician may enter any appropriate notes or instructions in the editable comment text box 860. In some embodiments of the present invention, editable comment box 860 may not include Personal Health Information (PHI). When the physician/clinician has completed all necessary updates, the edits will be written back to the database upon the physician/clinician initiating submission via submit button 870.

Figure 9:
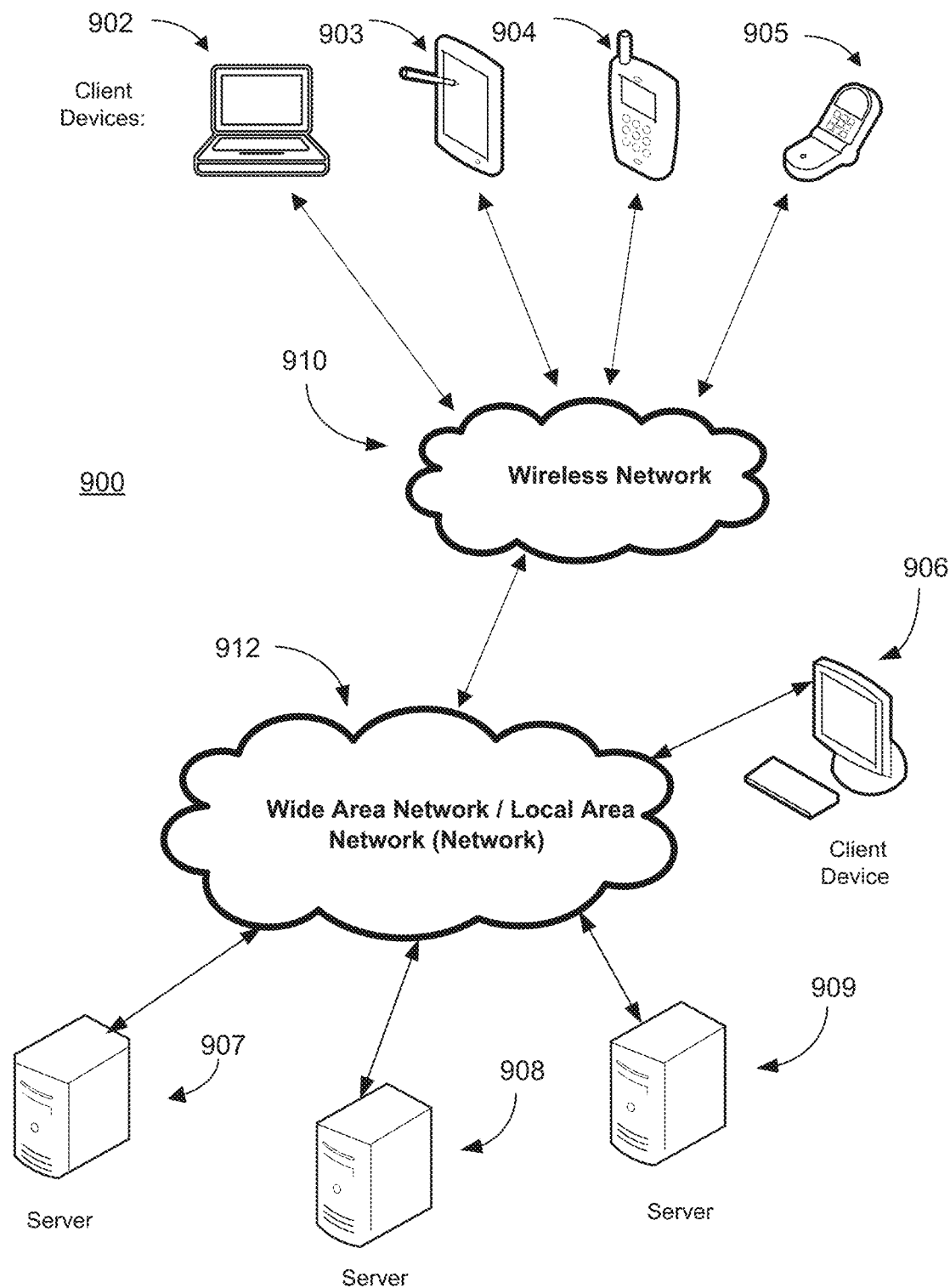
FIG. 9 illustrates a block diagram of a distributed computer system that can implement one or more aspects of an embodiment of the invention.

FIG. 9 illustrates components of one embodiment of an environment 900 in which the invention may be practiced. Not all the components may be required to practice the invention, and variations in the arrangement and type of the components may be made without departing from the spirit or scope of the invention. As shown, the system 900 includes one or more Local Area Networks ("LANs")/Wide Area Networks ("WANs") 912, one or more wireless networks 910, one or more wired or wireless client devices 906, mobile or other wireless client devices 902-906, servers 907-909, and may include or communicate with one or more data stores or databases. Various of the client devices 902-906 may include, for example, desktop computers, laptop computers, set top boxes, tablets, monitors, cell phones, smart phones, devices for interfacing with, or viewing dashboards or analytics relating to, EMR related systems or entities, etc. The servers 907-909 can include, for example, one or more application servers, content servers, search servers, Mirth or other HL7 Messaging servers, Database servers, database management or SQL servers, other servers relating to EMR related systems, etc.

Figure 10:
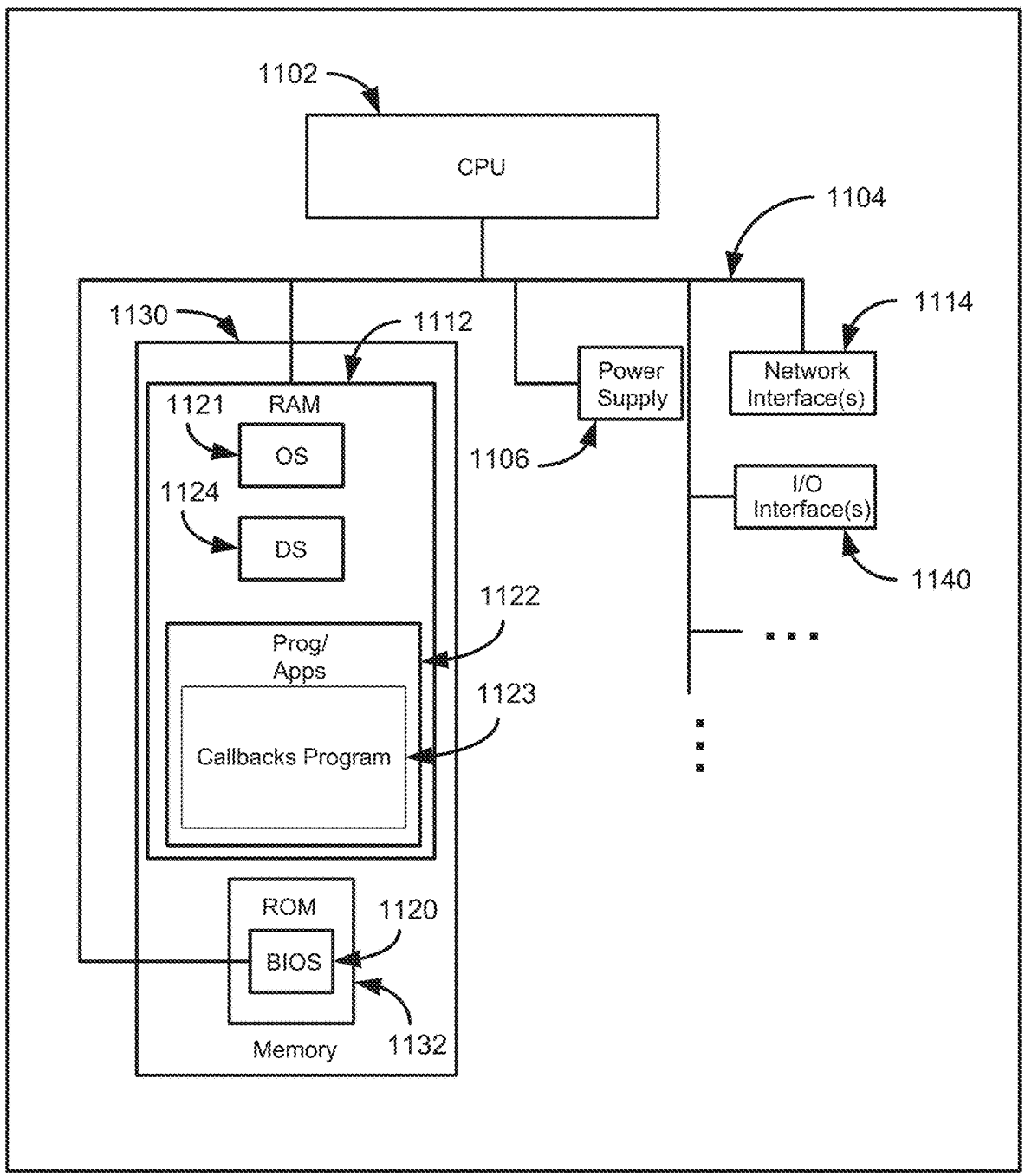
FIG. 10 illustrates a block diagram of an electronic device that can implement one or more aspects of an embodiment of the invention.

FIG. 10 illustrates a block diagram of an electronic device 1100 that can implement one or more aspects of EMR related systems and methods according to embodiments of the invention. Instances of the electronic device 1100 may include servers, e.g., servers 1007-1009, and client devices, e.g., client devices 1002-1006. In general, the electronic device 1100 can include a processor/CPU 1102, memory 1130, a power supply 1106, and input/output (I/O) components/devices 1140, e.g., microphones, speakers, displays, touchscreens, keyboards, mice, keypads, microscopes, GPS components, etc., which may be operable, for example, to provide graphical user interfaces, dashboards, etc.

A user may provide input via a touchscreen of an electronic device 1100. A touchscreen may determine whether a user is providing input by, for example, determining whether the user is touching the touchscreen with a part of the user's body such as his or her fingers. The electronic device 1100 can also include a communications bus 1104 that connects the aforementioned elements of the electronic device 1100. Network interfaces 1114 can include a receiver and a transmitter (or transceiver), and one or more antennas for wireless communications.

The processor 1102 can include one or more of any type of processing device, e.g., a Central Processing Unit (CPU), and a Graphics Processing Unit (GPU). Also, for example, the processor can be central processing logic, or other logic, may include hardware, firmware, software, or combinations thereof, to perform one or more functions or actions, or to cause one or more functions or actions from one or more other components. Also, based on a desired application or need, central processing logic, or other logic, may include, for example, a software-controlled microprocessor, discrete logic, e.g., an Application Specific Integrated Circuit (ASIC), a programmable/programmed logic device, memory device containing instructions, etc., or combinatorial logic embodied in hardware. Furthermore, logic may also be fully embodied as software.

The memory 1130, which can include Random Access Memory (RAM) 1112 and Read Only Memory (ROM) 1132, can be enabled by one or more of any type of memory device, e.g., a primary (directly accessible by the CPU) or secondary (indirectly accessible by the CPU) storage device (e.g., flash memory, magnetic disk, optical disk, and the like). The ROM 1132 can also include Basic Input/Output System (BIOS) 1120 of the electronic device.

The RAM can include an operating system 1121, data storage 1124, which may include one or more databases, and programs and/or applications 1122 and an EMR program 1123. The EMR program 1123 is intended to broadly include all programming, applications, algorithms, software and other and tools necessary to implement or facilitate methods and systems according to embodiments of the invention. Elements of the EMR program 1123 program may exist on a single server computer or be distributed among multiple computers, servers, devices or entities, or sites.

The power supply 1106 contains one or more power components and facilitates supply and management of power to the electronic device 1100.

The input/output components, including Input/Output (I/O) interfaces 1140, can include, for example, any interfaces for facilitating communication between any components of the electronic device 1100, components of external devices (e.g., components of other devices of the network or system 1100), and end users. For example, such components can include a network card that may be an integration of a receiver, a transmitter, a transceiver, and one or more input/output interfaces. A network card, for example, can facilitate wired or wireless communication with other devices of a network. In cases of wireless communication, an antenna can facilitate such communication. Also, some of the input/output interfaces 1140 and the bus 1104 can facilitate communication between components of the electronic device 1100, and in an example can ease processing performed by the processor 1102.

Where the electronic device 1100 is a server, it can include a computing device that can be capable of sending or receiving signals, e.g., via a wired or wireless network, or may be capable of processing or storing signals, e.g., in memory as physical memory states. The server may be an application server that includes a configuration to provide one or more applications.

Any computing device capable of sending, receiving, and processing data over a wired and/or a wireless network may act as a server, such as in facilitating aspects of implementations of EMR related systems and methods according to embodiments of the invention. Devices acting as a server may include devices such as dedicated rack-mounted servers, desktop computers, laptop computers, set top boxes, integrated devices combining one or more of the preceding devices, etc.

Servers may vary widely in configuration and capabilities, but they generally include one or more central processing units, memory, mass data storage, a power supply, wired or wireless network interfaces, input/output interfaces, and an operating system such as Windows Server, Mac OS X, Unix, Linux, FreeBSD, and the like.

A server may include, for example, a device that is configured, or includes a configuration, to provide data or content via one or more networks to another device, such as in facilitating aspects of an example EMR systems and methods according to embodiments of the invention. One or more servers may, for example, be used in hosting a Web site, such as the web site www.microsoft.com. One or more servers may host a variety of sites, such as, for example, business sites, informational sites, social networking sites, educational sites, wikis, financial sites, government sites, personal sites, and the like.

Servers may also, for example, provide a variety of services, such as Web services, third-party services, audio services, video services, email services, HTTP or HTTPS services, Instant Messaging (IM) services, Short Message Service (SMS) services, Multimedia Messaging Service (MMS) services, File Transfer Protocol (FTP) services, Voice Over IP (VOIP) services, calendaring services, phone services, and the like, all of which may work in conjunction with example aspects of EMR systems and methods according to embodiments of the invention. Content may include, for example, text, images, audio, video, and the like.

In example aspects of EMR systems and methods according to embodiments of the invention, client devices may include, for example, any computing device capable of sending and receiving data over a wired and/or a wireless network. Such client devices may include desktop computers as well as portable devices such as cellular telephones, smart phones, display pagers, Radio Frequency (RF) devices, Infrared (IR) devices, Personal Digital Assistants (PDAs), handheld computers, GPS-enabled devices tablet computers, monitors, sensor-equipped devices, laptop computers, set top boxes, wearable computers, integrated devices combining one or more of the preceding devices, and the like.

Client devices may range widely in terms of capabilities and features. For example, a cell phone, smart phone or tablet may have a numeric keypad and a few lines of monochrome Liquid-Crystal Display (LCD) display on which only text may be displayed. In another example, a Web-enabled client device may have a physical or virtual keyboard, data storage (such as flash memory or SD cards), accelerometers, gyroscopes, GPS or other location-aware capability, and a 2D or 3D touch-sensitive color screen on which both text and graphics may be displayed.

Client devices, such as client devices 1002-1006, for example, as may be used in example EMR systems and methods according to embodiments of the invention, may run a variety of operating systems, including personal computer operating systems such as Windows, iOS or Linux, and mobile operating systems such as iOS, Android, Windows Mobile, and the like. Client devices may be used to run one or more applications that are configured to send or receive data from another computing device. Client applications may provide and receive textual content, multimedia information, and the like. Client applications may perform actions such as viewing or interacting with analytics or dashboards, interacting with medical, patient-related, hospital or medical facility-related, EMR or EMR-related entities or systems, browsing webpages, using a web search engine, interacting with various apps stored on a smart phone, sending and receiving messages via email, SMS, or MMS, playing games, receiving advertising, watching locally stored or streamed video, or participating in social networks.

In example aspects of EMR systems and methods according to embodiments of the invention, one or more networks, such as networks 1010 or 1012, for example, may couple servers and client devices with other computing devices, including through wireless network to client devices. A network may be enabled to employ any form of computer readable media for communicating information from one electronic device to another. A network may include the Internet in addition to Local Area Networks (LANs), Wide Area Networks (WANs), direct connections, such as through a Universal Serial Bus (USB) port, other forms of computer-readable media, or any combination thereof. On an interconnected set of LANs, including those based on differing architectures and protocols, a router acts as a link between LANs, enabling data to be sent from one to another.

Communication links within LANs may include twisted wire pair or coaxial cable, while communication links between networks may utilize analog telephone lines, cable lines, optical lines, full or fractional dedicated digital lines including T1, T2, T3, and T4, Integrated Services Digital Networks (ISDNs), Digital Subscriber Lines (DSLs), wireless links including satellite links, optic fiber links, or other communications links known to those skilled in the art. Furthermore, remote computers and other related electronic devices could be remotely connected to either LANs or WANs via a modem and a telephone link.

A wireless network, such as wireless network 1010, as in example EMR systems and methods according to embodiments of the invention, may couple devices with a network. A wireless network may employ stand-alone ad-hoc networks, mesh networks, Wireless LAN (WLAN) networks, cellular networks, and the like.

A wireless network may further include an autonomous system of terminals, gateways, routers, or the like connected by wireless radio links, or the like. These connectors may be configured to move freely and randomly and organize themselves arbitrarily, such that the topology of wireless network may change rapidly. A wireless network may further employ a plurality of access technologies including 2nd (2G), 3rd (3G), 4th (4G) generation, Long Term Evolution (LTE) radio access for cellular systems, WLAN, Wireless Router (WR) mesh, and the like. Access technologies such as 2G, 2.5G, 3G, 4G, and future access networks may enable wide area coverage for client devices, such as client devices with various degrees of mobility. For example, a wireless network may enable a radio connection through a radio network access technology such as Global System for Mobile communication (GSM), Universal Mobile Telecommunications System (UMTS), General Packet Radio Services (GPRS), Enhanced Data GSM Environment (EDGE), 3GPP Long Term Evolution (LTE), LTE Advanced, Wideband Code Division Multiple Access (WCDMA), Bluetooth, 802.11b/g/n, and the like. A wireless network may include virtually any wireless communication mechanism by which information may travel between client devices and another computing device, network, and the like.

Internet Protocol (IP) may be used for transmitting data communication packets over a network of participating digital communication networks, and may include protocols such as TCP/IP, UDP, DECnet, NetBEUI, IPX, AppleTalk, and the like. Versions of the Internet Protocol include IPv4 and IPv6. The Internet includes local area networks (LANs), Wide Area Networks (WANs), wireless networks, and long-haul public networks that may allow packets to be communicated between the local area networks. The packets may be transmitted between nodes in the network to sites each of which has a unique local network address. A data communication packet may be sent through the Internet from a user site via an access node connected to the Internet. The packet may be forwarded through the network nodes to any target site connected to the network provided that the site address of the target site is included in a header of the packet. Each packet communicated over the Internet may be routed via a path determined by gateways and servers that switch the packet according to the target address and the availability of a network path to connect to the target site.

The header of the packet may include, for example, the source port (16 bits), destination port (16 bits), sequence number (32 bits), acknowledgement number (32 bits), data offset (4 bits), reserved (6 bits), checksum (16 bits), urgent pointer (16 bits), options (variable number of bits in multiple of 8 bits in length), padding (may be composed of all zeros and includes a number of bits such that the header ends on a 32 bit boundary). The number of bits for each of the above may also be higher or lower.

A "content delivery network" or "content distribution network" (CDN), as may be used in example EMR systems and methods according to embodiments of the invention, generally refers to a distributed computer system that comprises a collection of autonomous computers linked by a network or networks, together with the software, systems, protocols and techniques designed to facilitate various services, such as the storage, caching, or transmission of content, streaming media and applications on behalf of content providers. Such services may make use of ancillary technologies including, but not limited to, "cloud computing," distributed storage, DNS request handling, provisioning, data monitoring and reporting, content targeting, personalization, and business intelligence. A CDN may also enable an entity to operate and/or manage a third party's Web site infrastructure, in whole or in part, on the third party's behalf.

A Peer-to-Peer (or P2P) computer network relies primarily on the computing power and bandwidth of the participants in the network rather than concentrating it in a given set of dedicated servers. P2P networks are typically used for connecting nodes via largely ad hoc connections. A pure peer-to-peer network does not have a notion of clients or servers, but only equal peer nodes that simultaneously function as both "clients" and "servers" to the other nodes on the network.

One embodiment of the present invention includes systems, methods, and a non-transitory computer readable storage medium or media tangibly storing computer program logic capable of being executed by a computer processor.

While the present invention has been particularly described with respect to the illustrated embodiments, it will be appreciated that various alterations, modifications and adaptations may be made based on the present disclosure and are intended to be within the scope of the present invention. While the invention has been described in connection with what are presently considered to be the most practical and preferred embodiments, it is to be understood that the present invention is not limited to the disclosed embodiments but, on the contrary, is intended to cover various modifications and equivalent arrangements included within the scope of the appended claims.

What is claimed is:

1. A method for providing an interface configured to run on a user device, to enable at least one clinician to contact at least one patient for medical follow-up, the method comprising:
    extracting patient detail batch information at a pre-defined time interval for one or more past patients from an electronic medical records (EMR) database or other patient information database into a batch database operably connected to a machine learning model comprising one or more model features;
    constructing a real-time database from streams of real-time health care data, wherein at least one stream of real-time health care data is associated with the at least one patient in a current or recent medical encounter, wherein the at least one stream of real-time health care data associated with the at least one patient is parsed in real-time or near real-time to identify and extract specified EMR data comprising patient clinical data obtained during the current or recent medical encounter into the real-time database;
    calculating, using the machine learning model, a risk level for the one or more past patients in the batch database, wherein the risk level includes a risk assessment of an emergency department (ED) visit by the one or more past patients occurring within a specified time period, the one or more past patients includes the at least one patient, and the risk level for the at least one patient is calculated using the specified EMR data and historical and chronologically tracked demographic and EMR data including a number of previous ED visits within a specified time period and a reason for each previous ED visit, wherein the historical and chronologically tracked demographic and EMR data relates to information of the one or more past patients relevant to at least one particular analytical use case related to the current or recent medical visit, and one or more model features obtained from the machine learning model;
    creating, in real-time or near real-time, daily schedule information for the at least one clinician wherein the at least one patient is identified as a high-risk patient based on the calculated risk level; and
    generating a user interface configured for display at the user device to enable the at least one clinician to contact the at least one patient and record medical follow-up disposition information through the user interface displayed at the user device.

2. The method of claim 1, further comprising contacting the at least one patient via the user device of the at least one clinician.

3. The method of claim 2, further comprising masking a mobile phone number or other contact identifier of the at least one clinician with a hospital site number during the patient contact.

4. The method of claim 1, wherein the at least one high-risk patient is flagged using the machine learning model applied to patient detail batch information retrieved at a pre-defined time interval for one or more past patients from an electronic medical records (EMR) database or other patient information database.

5. The method of claim 1, further comprising generating a user interface enabling at least one user to manually update an assignment of the at least one clinician to the at least one patient.

6. The method of claim 1, further comprising generating a user interface enabling at least one medical site director to edit one or more callback target or provider attribution configurations.

7. A computer-implemented system for use with Electronic Medical Record (EMR) data associated with one or more patients, the system comprising:
    a parser engine configured to:
        receive, in real time or near real time relative to entry of EMR data into an EMR system, health care data messages including the EMR data;

construct a real-time database from the health care data messages, wherein at least one stream of health care data messages is associated with at least one patient in a current or recent medical encounter; and using parsing logic, parse, in real time or near real time relative to entry of the EMR data, the health care data messages to identify and extract specified EMR data comprising patient clinical data of the at least one patient obtained during the current or recent medical encounter into the real-time database;

one or more databases, configured to, in real time or near real time relative to entry of the EMR data:

receive and store the extracted specified EMR data;

extract patient detail batch information at a pre-defined time interval for one or more past patients from an EMR database into a batch database operably connected to a machine learning model comprising one or more model features; and calculate, using the machine learning model, a risk level for the one or more past patients in the batch database, wherein the risk level includes a risk assessment of an emergency department (ED) visit by the one or more past patients occurring within a specified time period, the one or more past patients includes the at least one patient, and the risk level for the at least one patient is calculated using the specified EMR data and historical and chronologically tracked demographic and EMR data including a number of previous ED visits within a specified time period and a reason for each previous ED visit, wherein the historical and chronologically tracked demographic and EMR data relates to information of the one or more past patients relevant to at least one particular analytical use case related to the current or recent medical visit, and one or more model features;

an analytics and presentation engine configured to generate in real time or near real time, a graphical user interface for display on a user device that presents specified analytic results data determined from analysis of the extracted specified EMR data in real time or near real time relative to entry of the EMR data, the graphical user interface comprising:

a list of one or more patients currently or recently admitted to and discharged from an emergency department of a medical facility or hospital, wherein the list of patients is associated with the at least one clinician and is determined using the extracted specified EMR data wherein the at least one patient is identified in the list of one or more patients as a high-risk patient based on the calculated risk level; and a contact identifier associated with the at least one patient for the at least one clinician to contact the at least one patient.

8. The system of claim 7, further comprising a communication interface to connect a user device of a patient on the patient list of the at least one clinician via the user device of the at least one clinician.

9. The system of claim 8, wherein the communication interface is configured to enable the at least one clinician to mask a mobile phone number or other contact identifier of the at least one clinician with a hospital site number during the patient contact.

10. The system of claim 7, wherein the at least one high-risk patient is flagged using the machine learning model applied to patient detail batch information retrieved at a pre-defined time interval for one or more past patients from an electronic medical records (EMR) database or other patient information database.

11. The system of claim 10, wherein the other patient information database comprises a billing database or a scheduling database.

12. The system of claim 7, wherein the at least one high-risk patient is determined by calculating a risk of revisit of the at least one high-risk patient to a hospital emergency department based on the extracted specified EMR data.

13. The system of claim 7, wherein the graphical user interface further comprises an interface configured to enable the at least one user to manually update medical disposition information of the at least one patient or an assignment of the at least one clinician to the at least one patient.

14. The system of claim 7, wherein the graphical user interface further comprises an interface configured to enable at least one medical site director to edit one or more callback target or provider attribution configurations.

15. A non-transitory computer readable medium storing instructions to generate a user interface configured to enable at least one clinician to contact at least one patient for medical follow-up, wherein the instructions upon execution by a processor perform:

extracting patient detail batch information at a pre-defined time interval for one or more past patients from an electronic medical records (EMR) database or other patient information database into a batch database operably connected to a machine learning model comprising one or more model features;

constructing a real-time database from streams of real-time health care data, wherein at least one stream of real-time health care data is associated with the at least one patient in a current or recent medical encounter, wherein the at least one stream of real-time health care data is parsed in real-time or near real-time to identify and extract specified EMR data comprising patient clinical data obtained during the current medical encounter into the real-time database;

calculating, using the machine learning model, a risk level for the one or more past patients in the batch database, wherein the risk level includes a risk assessment of an emergency department (ED) visit by the one or more past patients occurring within a specified time period, the one or more past patients includes the at least one patient, and the risk level for the at least one patient is calculated using the specified EMR data and historical and chronologically tracked demographic and EMR data including a number of previous ED visits within a specified time period and a reason for each previous ED visit, wherein the historical and chronologically tracked demographic and EMR data relates to information of the one or more past patients relevant to at least one particular analytical use case related to the current or recent medical visit, and one or more model features obtained from the machine learning model;

creating in real-time or near real-time, daily schedule information for the at least one clinician wherein the at least one patient is identified as a high-risk patient based on the calculated risk levels; and generating a user interface configured for display at the user device to enable the at least one clinician to contact the at least one patient and record medical follow-up disposition information.

16. The non-transitory computer readable medium of claim 15, further comprising contacting the at least one patient via the user device of the at least one clinician.

17. The non-transitory computer readable medium of claim 16, further comprising masking a mobile phone number or other contact identifier of the at least one clinician with a hospital site number during the patient contact.

18. The non-transitory computer readable medium of claim 15, wherein at least one high-risk patient is flagged by using the machine learning model applied to patient detail batch information retrieved at a pre-defined time interval for the one or more past patients from the electronic medical records (EMR) database or other patient information database.

19. The non-transitory computer readable medium of claim 15, further comprising generating a user interface enabling the at least one user to manually update an assignment of the at least one clinician to the at least one patient.

20. The non-transitory computer readable medium of claim 15, further comprising generating a user interface enabling at least one medical site director to edit one or more callback target or provider attribution configurations.

* * * * *